(12) United States Patent
Arnold et al.

(10) Patent No.: US 10,786,448 B2
(45) Date of Patent: Sep. 29, 2020

(54) CHEWING GUM COMPOSITION COMPRISING POLYHEXANIDE

(71) Applicants: Christian Arnold, Ebersberg (DE); Armin Armani, Grünwald (DE)

(72) Inventors: Christian Arnold, Ebersberg (DE); Armin Armani, Grünwald (DE)

( * ) Notice: Subject to any disclaimer, the term of this patent is extended or adjusted under 35 U.S.C. 154(b) by 0 days.

(21) Appl. No.: 16/251,702

(22) Filed: Jan. 18, 2019

(65) Prior Publication Data
US 2019/0224116 A1    Jul. 25, 2019

Related U.S. Application Data

(60) Provisional application No. 62/618,836, filed on Jan. 18, 2018.

(51) Int. Cl.
| *A61K 9/68* | (2006.01) |
| *A61K 31/785* | (2006.01) |
| *A61K 9/00* | (2006.01) |
| *A61K 47/02* | (2006.01) |
| *A61P 31/02* | (2006.01) |
| *A61P 31/00* | (2006.01) |

(52) U.S. Cl.
CPC .......... *A61K 9/0058* (2013.01); *A61K 9/0063* (2013.01); *A61K 31/785* (2013.01); *A61K 47/02* (2013.01); *A61P 31/00* (2018.01); *A61P 31/02* (2018.01)

(58) Field of Classification Search
None
See application file for complete search history.

(56) References Cited

U.S. PATENT DOCUMENTS

| | | | |
|---|---|---|---|
| 4,271,197 A | 6/1981 | Hopkins et al. | |
| 4,569,837 A | 2/1986 | Suzuki et al. | |
| 4,764,377 A | 8/1988 | Goodson | |
| 4,892,736 A | 1/1990 | Goodson | |
| 5,002,769 A | 3/1991 | Friedman | |
| 5,223,282 A | 6/1993 | Patel et al. | |
| 6,200,550 B1 | 3/2001 | Masterson et al. | |
| 6,770,264 B2 | 8/2004 | Stier et al. | |
| 7,056,541 B1 | 6/2006 | Stahl | |
| 9,820,918 B2 | 11/2017 | Arnold et al. | |
| 2002/0004068 A1 | 1/2002 | Di Drusco | |
| 2003/0049208 A1 | 3/2003 | Ream et al. | |
| 2004/0028772 A1* | 2/2004 | Andersen | A23G 4/02 426/3 |
| 2004/0115137 A1 | 6/2004 | Verrall et al. | |
| 2005/0048005 A1 | 3/2005 | Stockel | |
| 2006/0034897 A1* | 2/2006 | Boghani | A23G 3/0017 424/440 |
| 2007/0053848 A1 | 3/2007 | Stockel | |
| 2007/0140990 A1* | 6/2007 | Fetissova | A61K 8/21 424/50 |
| 2008/0014224 A1 | 1/2008 | Boyd et al. | |
| 2009/0214606 A1 | 8/2009 | Bujard et al. | |
| 2009/0324454 A1 | 12/2009 | Nakano et al. | |
| 2010/0284946 A1* | 11/2010 | Steenberg | A61K 9/0058 424/48 |
| 2012/0107258 A1 | 5/2012 | Kuhn et al. | |
| 2012/0225111 A1 | 9/2012 | Scholz | |
| 2014/0303100 A1 | 10/2014 | Winston et al. | |
| 2015/0297468 A1* | 10/2015 | Arnold | A61K 9/06 424/48 |
| 2018/0092813 A1 | 4/2018 | Arnold et al. | |

FOREIGN PATENT DOCUMENTS

| | | |
|---|---|---|
| DE | 202009000862 U1 | 4/2009 |
| DE | 102009005865 A1 | 7/2010 |
| DE | 102012007212 A1 | 10/2013 |
| DE | 202013000446 U1 | 10/2013 |
| DE | 102012019194 A1 | 4/2014 |
| DE | 202015104316 U1 | 8/2016 |
| EP | 1514477 A2 | 3/2005 |
| EP | 1227820 B1 | 4/2006 |
| EP | 1685843 A1 | 8/2006 |
| EP | 1964541 A1 | 9/2008 |
| EP | 1964543 A1 | 9/2008 |
| EP | 1917982 B1 | 4/2010 |
| EP | 2181721 A2 | 5/2010 |
| EP | 2046264 B1 | 8/2014 |
| EP | 2896396 A1 | 7/2015 |
| EP | 2874600 B1 | 6/2016 |
| EP | 2896395 B1 | 10/2016 |
| EP | 3127538 A1 | 2/2017 |
| EP | 3 134 075 A2 | 3/2017 |
| EP | 2079311 B1 | 3/2017 |
| EP | 2512407 B1 | 11/2017 |
| EP | 3300794 A2 | 4/2018 |

(Continued)

OTHER PUBLICATIONS

Espacenet search for polyhexanide_Sep. 20, 2019 (Year: 2019).*
Zaugg, L.K., et al., "Antimicrobial activity of short- and medium-term applications of polyhexamethylene biguanide, chlorhexidine digluconate and calcium hydroxide in infected immature bovine teeth in vitro," Dental Traumatology 30:326-331, John Wiley & Sons, United States (2014).
International Search Report and Written Opinion for International Application No. PCT/IB2019/050438, European Patent Office, Netherlands, dated May 29, 2019, 10 pages.
Rohrer, N. et al., "Antimicrobial efficacy of 3 oral antiseptics containing Octenidine, Polyhexamethylene Biguanide, or Citroxx: Can Chlorhexidine be Replaced?" Infection Control & Hospital Epidemiology 31:733-739 (2010).

(Continued)

*Primary Examiner* — Michael P Cohen
(74) *Attorney, Agent, or Firm* — Sterne, Kessler, Goldstein & Fox P.L.L.C.

(57) ABSTRACT

This disclosure describes a chewing gum composition comprising polyhexanide for the treatment and/or prevention of an infectious disease in the oral cavity. The present disclosure also describes a chewing gum composition formulated for the controlled release of polyhexanide and optionally, at least one additional water-soluble antiseptic agent.

20 Claims, 8 Drawing Sheets

(56) References Cited

FOREIGN PATENT DOCUMENTS

| | | |
|---|---|---|
| EP | 2836196 B1 | 6/2019 |
| EP | 3096750 B1 | 7/2019 |
| WO | WO 94/14424 A1 | 7/1994 |
| WO | WO 99/44436 A1 | 9/1999 |
| WO | WO 2005107456 A2 | 11/2005 |
| WO | WO 2006120135 A1 | 11/2006 |
| WO | WO 2006128269 A2 | 12/2006 |
| WO | WO 2006128270 A2 | 12/2006 |
| WO | WO 2007062995 A2 | 6/2007 |
| WO | WO 2008061816 A2 | 5/2008 |
| WO | WO 2008141416 A1 | 11/2008 |
| WO | WO 2012145307 A1 | 10/2012 |
| WO | WO-2014044869 A3 | 3/2014 |
| WO | WO 2014078801 A1 | 5/2014 |
| WO | WO 2014092999 A1 | 6/2014 |
| WO | WO 2014153356 A1 | 9/2014 |
| WO | WO 2014186742 A2 | 11/2014 |
| WO | WO 2015038689 A2 | 3/2015 |
| WO | WO 2016065443 A1 | 5/2016 |
| WO | WO 2016081295 A1 | 5/2016 |
| WO | WO 2017028977 A1 | 2/2017 |
| WO | WO 2017029070 A1 | 2/2017 |
| WO | WO 2017189589 A1 | 11/2017 |
| WO | WO 2018031357 A1 | 2/2018 |
| WO | WO 2018158763 A1 | 9/2018 |
| WO | WO 2018217351 A1 | 11/2018 |
| WO | WO 2019202015 A1 | 10/2019 |

OTHER PUBLICATIONS

Rosin, M. et al., "The effect of a polyhexamethylene biguanide mouthrinse compared to an essential oil rinse and a chlorhexidine rinse on bacterial counts and 4-day plaque regrowth," J Clin Periodontol 29(5):392-399 (2002).

Tikus, H.W., "Topical gels containing Chlorhexidine, Vantocil, Fluorophene and animal caries," Helv Odontol Acta 17:105-108 (1973).

Zaugg, L.K., et al., "Antimicrobial activity of short and medium-term application s of polyhexamethylene biguanide, chlorhexidine digluconate and calcium hydroxide in infected immature bovine teeth in vitro," Dent Traumatol 30:326-331 (2013).

English languages abstracts for foreign patent publications, DE102009005865A1, DE202009000862U1, DE202013000446U1, DE202015104316U1, EP1917982 A1, EP2181721A2, EP2836196A1 Abstract of corresponding DE102012007212A1, EP2874600B1 Abstract of corresponding DE202013000446U1, WO2008061816A2, WO2016065443A1 and WO2017028977A1, 3 pages.

\* cited by examiner

CHEWING GUM COMPOSITION COMPRISING POLYHEXANIDE

FIELD

This disclosure describes a chewing gum composition comprising polyhexanide for the treatment and/or prevention of an infectious disease in the oral cavity. The present disclosure also describes a chewing gum composition formulated for the controlled release of polyhexanide and optionally, at least one additional water-soluble antiseptic agent.

BACKGROUND

Pharmaceutical compositions which exhibit a release of agents and which can be introduced into the periodontal cavity and slowly release an antimicrobial agent have been developed. For example, U.S. Pat. Nos. 4,764,377 and 4,892,736 disclose the introduction of tetracycline into non-degradable polymeric fibers which can be wound around the teeth and release the antibiotic in the periodontal cavity over several days. However, the fibers must be fixed in their place with an adhesive and be removed again at the end of the treatment method.

U.S. Pat. No. 4,569,837 discloses the use of water-soluble polymeric substances as a polymeric matrix for a periodontal implant.

U.S. Pat. No. 5,002,769 discloses a biodegradable system for oral administration with delayed release for treating periodontal diseases. The agent is embedded into a matrix of hydrolyzed gelatin which is cross-linked with glutaraldehyde.

U.S. Pat. No. 9,820,918 discloses an oral delivery system for the treatment and/or prevention of infectious pathological changes that includes compositions comprising polyhexanide.

BRIEF SUMMARY

This disclosure provides a chewing gum composition comprising polyhexanide, wherein the chewing gum composition comprises a chewing gum core, wherein the chewing gum core comprises between about 0.05% and about 10% polyhexanide by weight and wherein the weight percentage of the total chewing gum core that is water-insoluble is between about 15% and about 60%.

In some embodiments, the chewing gum core comprises between about 0.01% and about 5% polyhexanide by weight.

In some embodiments, the chewing gum core is formed using a compression force of between about 1 kN/cm$^2$ and about 50 kN/cm$^2$.

In some embodiments, the chewing gum core is formed using a compression force of between about 5 kN/cm$^2$ and about 50 kN/cm$^2$.

In some embodiments, the chewing gum core is formed using a compression force of between about 20 kN/cm$^2$ and about 50 kN/cm$^2$.

In some embodiments, the chewing gum composition further comprises a fluoride salt. In some embodiments, the fluoride salt is selected from the group consisting of sodium fluoride, potassium fluoride, stannous fluoride, potassium stannous fluoride, lithium fluoride, ammonium fluoride, tin fluoride, indium fluoride, zirconium fluoride, copper fluoride, nickel fluoride, palladium fluoride, zinc fluoride, ammonium fluoride, stannous chloroflouride, sodium monofluorophosphate, ammonium monofluorophosphate, aluminum monofluorophosphate, and mixtures thereof.

In some embodiments, the chewing gum core comprises between about 0.001% and about 0.10% of the fluoride salt by weight.

In some embodiments, the chewing gum composition further comprises at least one sweetener. In some embodiments, the at least one sweetener is selected from the group consisting of saccharin, aspartame, acesulfame potassium, sucralose, alitame, sorbitol, mannitol, maltitol, xylitol, isomalt, erythritol, lactitol, neotame, advantame, stevia, and hydrogenated starch hydrolysate.

In some embodiments, the chewing gum core comprises between about 0.05% to about 10% of the at least one sweetener by weight.

In some embodiments, the chewing gum composition further comprises at least one flavor. In some embodiments, the at least one flavor is selected from the group consisting of a citrus, a fruit, peppermint, spearmint, wintergreen, cinnamon, cocoa, vanilla, licorice, menthol, *eucalyptus*, anise, and almond.

In some embodiments, the chewing gum core comprises between about 0.05% to about 10% of the at least one flavor by weight.

In some embodiments, the chewing gum composition, further comprises at least one filler. In some embodiments, the at least one filler is selected from the group consisting of calcium carbonate, magnesium carbonate, magnesium stearate, magnesium silicate, aluminum silicate, calcium phosphate, talc, dicalcium phosphate, and sodium carbonate.

In some embodiments, the chewing gum core comprises between about 0.05% to about 10% of the at least one filler by weight.

In some embodiments, the chewing gum composition further comprises at least one gum base. In some embodiments, the at least one gum base is a synthetic gum base or a natural gum base.

In some embodiments, the chewing gum core comprises between about 5% to about 95% of the at least one gum base by weight.

In some embodiments, the at least one gum base in the chewing gum composition is a synthetic gum base selected from the group consisting of polyvinyl acetate, polyvinyl laurate, polyvinyl alcohol, polyvinyl pyrrolidone, polyisobutylene, butyl rubber, and styrene butadiene rubber.

In some embodiments, the at least one gum base in the chewing gum composition is HEALTH IN GUM PWD 03 and PG ALEX 13 T.

In some embodiments, the chewing gum composition further comprises a fluoride salt, at least one sweetener, at least one flavor, at least one filler, and at least one gum base.

In some embodiments, less than 50% of the total polyhexanide content in the chewing gum composition is released within the first 2 minutes from initiation of a chewing process.

In some embodiments, less than 25% of the total polyhexanide content in the chewing gum composition is released within the first 2 minutes from initiation of a chewing process.

In some embodiments, greater than 75% of the total polyhexanide content in the chewing gum composition is released within the first 15 minutes from initiation of a chewing process.

In some embodiments, the polyhexanide has a weight average molecular weight of between about 1600 g/mol and about 3600 g/mol.

In some embodiments, the total weight of the chewing gum composition is between about 1.4 g and about 2.5 g, the total weight of the polyhexanide is between about 2 mg and 50 mg, and the polyhexanide is in the chewing gum core.

In some embodiments, the chewing gum composition further comprises at least one coating layer.

In some embodiments, the total chewing gum core that is water-insoluble is between about 20% and about 50%.

In some embodiments, the total chewing gum core that is water-insoluble is between about 27% and about 40%.

This disclosure provides a method of treating an infectious disease of the oral cavity, comprising administering the chewing gum composition.

In some embodiments, the infectious disease of the oral cavity is selected from the group consisting of gingivitis, periodontitis, peri-implantitis, dental caries, mycosis, laryngitis, pharyngitis, and halitosis.

In some embodiments, the chewing gum composition is administered between about one and about ten times per day.

In some embodiments, the chewing gum composition is administered between about one and about four times per day.

In some embodiments, the chewing gum composition is administered for treatment of a viral infection.

This disclosure provides a method of preparing a chewing gum composition, wherein greater than 75% of the total polyhexanide content in the chewing gum composition is released within 15 minutes from initiation of a chewing process.

This disclosure also provides a chewing gum composition comprising polyhexanide, wherein the chewing gum composition comprises a chewing gum core, wherein the chewing gum core comprises between about 0.05% and about 10% polyhexanide by weight, and wherein the chewing gum core is formed using a compression force between about 5 kN/cm$^2$ and about 50 kN/cm$^2$.

In some embodiments, the chewing gum core is formed using a compression force between about 20 kN/cm$^2$ and about 50 kN/cm$^2$.

This disclosure also provides a chewing gum composition comprising polyhexanide, wherein the chewing gum composition comprises a chewing gum core, wherein the chewing gum core comprises between about 0.05% and about 10% polyhexanide by weight, and wherein the total weight of the chewing gum composition is between about 1.4 g and about 2.5 g.

In some embodiments, the total weight of chewing gum composition is between about 1.6 g and about 2.1 g.

This disclosure also provides a chewing gum composition comprising polyhexanide, wherein the chewing gum composition comprises a chewing gum core, wherein the chewing gum core comprises between about 0.05% and about 10% polyhexanide by weight, and wherein less than 30% of the total polyhexanide content in the chewing gum composition is released within the first 2 minutes from initiation of a chewing process.

In some embodiments, less than 50% of the total polyhexanide content in the chewing gum composition is released within the first 4 minutes from initiation of a chewing process.

In some embodiments, greater than 75% of the total polyhexanide content in the chewing gum composition is released within the first 15 minutes from initiation of a chewing process.

BRIEF DESCRIPTION OF THE DRAWINGS

The above-mentioned features and objects of this disclosure will become more apparent with reference to the following description taken in conjunction with the accompanying drawings.

As shown in FIG. 4, the fastest release was obtained with samples having the lowest PHMB concentration.

DETAILED DESCRIPTION

Figure 1:
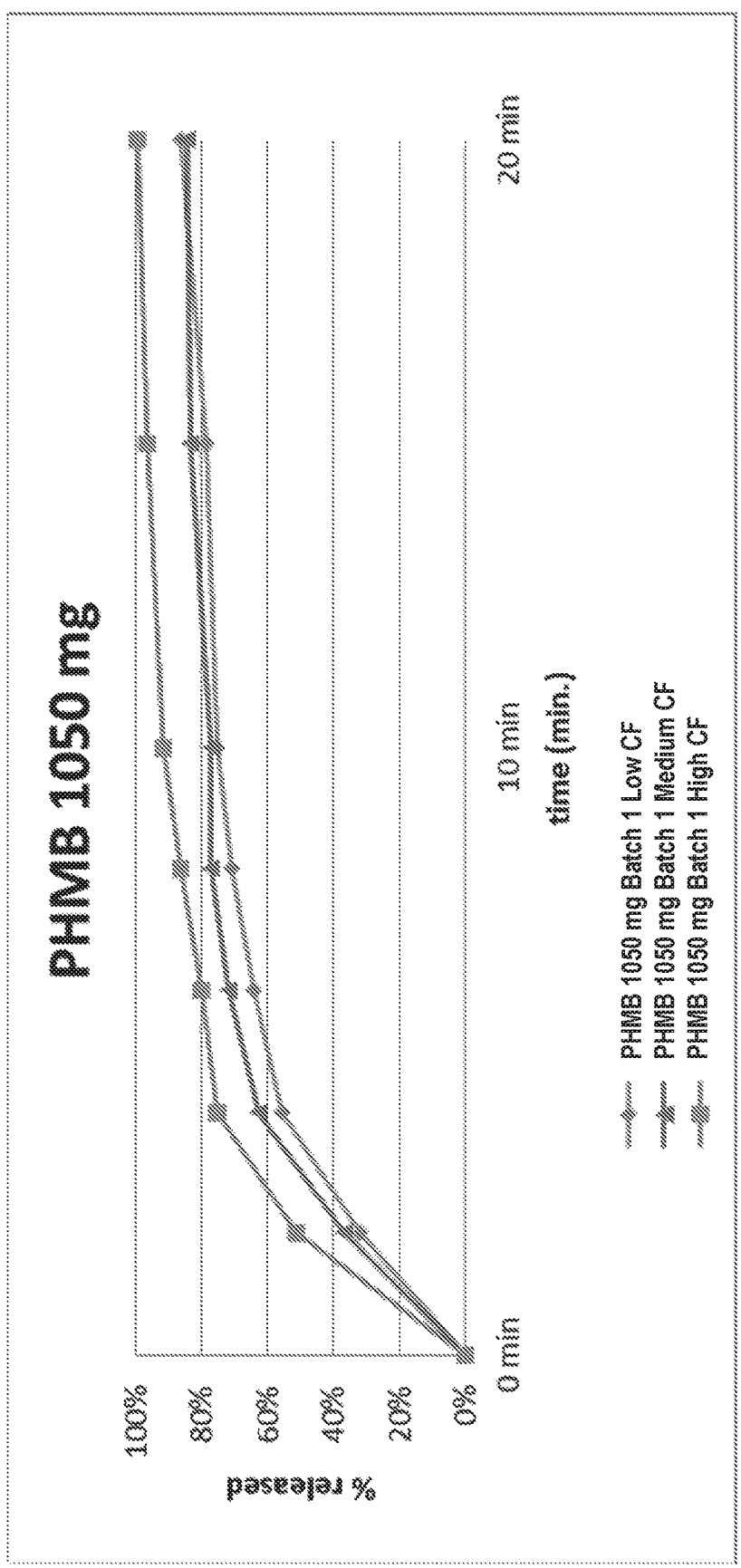
FIG. 1 is a line graph showing the percentage of polyhexanide (PHMB) released over time for 1050 mg samples of PHMB chewing gums having the composition of Batch 1 as described in TABLE 5 in Example 7, compressed at three different average compression forces (CF): 678 kg/cm$^2$ (Low CF), 1682 kg/cm$^2$ (Medium CF), and 2910 kg/cm$^2$ (High CF).

As used in this specification and the appended claims, the singular forms "a," "an," and "the" include plural referents unless the context clearly dictates otherwise.

The term "about" as used herein indicates the value of a given quantity varies by +10% of the value. For example, "about 10" encompasses a range of 9 to 11, inclusive.

As used herein, the term "chewing gum composition" refers to all chewable gum products. In some embodiments, the chewing gum composition is a chewing gum composition comprising a gum base, wherein the gum base does not significantly disintegrate in the mouth. A gum base does not significantly disintegrate in the mouth when at least 85% of the gum base does not disintegrate after 15 minutes in the mouth. In some embodiments, a gum base does not significantly disintegrate in the mouth when at least 90% of the gum base does not disintegrate after 15 minutes in the mouth. In some embodiments, a gum base does not significantly disintegrate in the mouth when at least 95% of the gum base does not disintegrate after 15 minutes in the mouth.

As used herein, the term "antibacterially effective amount" refers to an amount effective to kill bacteria or inhibit the growth of bacteria. The term "inhibit" as used herein, refers to a detectable reduction and/or elimination of a biological activity exhibited in the absence of the active ingredient. An antibacterially effective amount can be determined by counting the number of bacterial colonies on an agar plate before and after application of an active ingredient. An antibacterially effective amount is an amount of active ingredient that shows a reduction in the number of bacterial colonies by 50% when measured 48 hours after application under anaerobic and aerobic conditions.

As used herein, the term "treatment" refers to reducing or alleviating symptoms in a subject, preventing symptoms from worsening or progressing, inhibition or elimination of the causative agent, or prevention of the infection or disorder caused by the germs in a subject. In some embodiments, the germ is a bacteria. In some embodiments, the germ is a virus. In some embodiments, the germ is a fungus.

As used herein, the term "controlled release" is intended to mean the release of an active ingredient from a gum by the aid of active chewing of the gum in the oral cavity of the subject, whereby the active chewing controls the amount of substance released.

As used herein, the term "slow release" is intended to mean that the active ingredient is released from the gum by chewing over a period of time. In some embodiments, the "slow release" of an active ingredient is over a time between about 1 minute and about 60 minutes.

As used herein, the term "chewing gum core" refers to a chewing gum composition without any coating(s). The chewing gum core can be used as the final product, i.e., the use of coating(s) is optional.

Chewing Gum Compositions

In some embodiments, the chewing gum composition comprises or consists of a chewing gum core and at least one coating layer. In some embodiments, the chewing gum core comprises or consists of a gum base, an active ingredient, and other additives.

Traditional chewing gums can be highly cariogenic because of their high sugar content, but they also massage the gingiva and the salivary glands in case of dry mouth. Chewing gums can also be refreshing, vitalizing, and thirst-quenching owing to the added flavorings.

In some embodiments, the chewing gum composition is used to support teeth and mouth hygiene and for the treatment and prevention of infectious diseases in the oral cavity. It is particularly suited for "on-the-go" use, when there is no opportunity to brush the teeth.

In some embodiments, the chewing gum composition can be used in a method of treating or preventing an infectious disease in the oral cavity. In some embodiments, the chewing gum composition can be used in a method of treating or preventing an infectious disease in the oral cavity selected from the group consisting of gingivitis, periodontitis, peri-implantitis, dental caries, mycosis, laryngitis, pharyngitis, and halitosis.

In some embodiments, the chewing gum composition can be used in a method of treating or preventing a viral infection. In some embodiments, the viral infection is selected from the group consisting of African Swine Fever Viruses, Arbovirus, Adenoviridae, Arenaviridae, Arterivirus, Astroviridae, Baculoviridae, Bimaviridae, Bimaviridae, Bunyaviridae, Calicivirdae, Caulimoviridae, Circoviridae, Coronaviridae, Cystoviridae, Dengue, EBV, HIV, Deltaviridae, Filviridae, Filoviridae, Flaviviridae, Hepadnaviridae (Hepatitis), HI-erpesviridae (such as, Cytomegalovirus, Herpes Simplex, Herpes Zoster), Iridoviridae, Mononegavirus (e.g., Paramyxoviridae, Morbillivirus, Rhabdoviridae), Myoviridae, Orthonmyxoviridae (e.g., Influenza A, Influenza B, and parainfluenza), Papilorma virus, Papovaviridae, Paramyxoviridae, Prions, Parvoviridae, Phycodnaviridae, Picornaviridae (e.g. Rhinovirus, Poliovirus), Poxviridae (such as Smallpox or Vaccinia), Potyviridae, Reoviridae (e.g., Rotavirus), Retroviridae (HTLV-I, HTLV-II, Lentivirus), Rhabdoviridae, Tectiviridae, Togaviridae (e.g., Rubivirus), or viruses which cause the common cold.

By delivering polyhexanide in the form of a chewing gum, the polyhexanide may reach the site of action, in particular the gingival pockets/sulci, in a particularly effective manner. The chewing process presses the chewing gum into the gingival pocket/sulcus, where the polyhexanide is then released onto the gingival pocket/sulcus or onto exposed dental surfaces. In some embodiments, polyhexanide is released and/or dissolved near dental surfaces and/or gingival pockets/sulci, which may result in a high local concentration of polyhexanide at the treatment site. In some embodiments, the high local concentration of polyhexanide at the treatment site is at least 50% of the total weight of polyhexanide in the chewing gum composition. In some embodiments, the high local concentration of polyhexanide at the treatment site is at least 70% of the total weight of polyhexanide in the chewing gum composition. In some embodiments, the concentration of polyhexanide released at the treatment site is greater when polyhexanide is delivered in the form of a chewing gum compared to delivery in the form of a mouthwash.

In some embodiments, the chewing gum composition comprises between about 2 mg and about 50 mg of polyhexanide. In some embodiments, the chewing gum composition comprises between about 2 mg and about 50 mg, about 2 mg and about 30 mg, about 2 mg and about 25 mg, about 2 mg and about 20 mg, about 2 mg and about 15 mg, about 2 mg and about 10 mg, about 2 mg and about 5 mg, about 5 mg and about 50 mg, about 5 mg and about 30 mg, about 5 mg and about 25 mg, about 5 mg and about 20 mg, about 5 mg and about 15 mg, about 5 mg and about 10 mg, about 10 mg and about 50 mg, about 10 mg and about 30 mg, about 10 mg and about 25 mg, about 10 mg and about 20 mg, about 10 mg and about 15 mg, about 15 mg and about 50 mg, about 15 mg and about 30 mg, about 15 mg and about 25 mg, about 15 mg and about 20 mg, about 20 mg and about 50 mg, about 20 mg and about 30 mg, about 20 mg and about 25 mg, about 25 mg and about 50 mg, about 25 mg and about 30 mg of polyhexanide, or about 30 mg and about 50 mg. In some embodiments, the chewing gum composition comprises between about 20 mg and about 25 mg of polyhexanide.

In some embodiments, the chewing gum composition is administered to a subject in need thereof. In some embodiments, the chewing gum composition is administered between about 1 and about 10 times per day. In some embodiments, the chewing gum composition is administered between about 1 and about 10, about 1 and about 8, about 1 and about 6, about 1 and about 4, about 1 and about 2, about 2 and about 10, about 2 and about 8, about 2 and about 6, about 2 and about 4, about 4 and about 10, about 4 and about 8, about 4 and about 6, about 6 and about 10, about 6 and about 8, or about 8 and about 10 times per day. In some embodiments, the chewing gum composition is administered between about 1 and about 4 times per day.

Gum Base

The gum base can be any gum base known to those of skill in the art. In some embodiments, the gum base is a natural gum base or a synthetic gum base. In certain embodiments, the gum base comprises water-insoluble polymers which do not disintegrate during chewing. In some embodiments, the water-insoluble content is the total amount of water-insoluble polymers which do not disintegrate during chewing.

In some embodiments, the weight percentage of water-insoluble polymers based on the total weight of the chewing gum core is between about 15% and about 60%. In some embodiments, the weight percentage of water-insoluble polymers based on the total weight of the chewing gum core is between about 15% and about 60%, about 15% and about 50%, about 15% and about 40%, about 15% and about 30%, about 15% and about 27%, about 15% and about 25%, about 15% and about 20%, 20% and about 60%, about 20% and about 50%, about 20% and about 40%, about 20% and about 30%, about 20% and about 27%, about 20% and about 25%, about 25% and about 60%, about 25% and about 50%, about 25% and about 40%, about 25% and about 30%, about 25% and about 27%, about 27% and about 60%, about 27% and about 50%, about 27% and about 40%, about 27% and about 30%, about 30% and about 60%, about 30% and about 50%, about 30% and about 40%, about 40% and about 60%, about 40% and about 50%, or about 50% and about 60%.

In some embodiments, the gum base is a natural gum base. In some embodiments, the gum base is a natural gum base selected from the group consisting of chicle, gutta-percha, latex, a benzoin resin, or gum arabic.

In some embodiments, the gum base is a synthetic gum base. In some embodiments, the synthetic gum base is an elastomer selected from the group consisting of polyisobutylene, polybutadiene, polybutadiene styrene, polyisobutylene, polyvinylacetate, isoprene, polyvinyl ether, polyethylene, and combinations thereof.

In some embodiments, the chewing gum composition comprises at least one gum base. In some embodiments, chewing gum composition comprises 1, 2, 3, 4, or 5 gum bases. In some embodiments, the chewing gum composition comprises 2 gum bases.

In some embodiments, the chewing gum composition comprises between about 100 mg and about 10 grams of gum base. In some embodiments, the chewing gum composition comprises between about 100 mg and about 10 g, about 100 mg and about 5 g, about 100 mg and about 2.5 g, about 100 mg and about 1.4 g, about 100 mg and about 1 g, about 100 mg and about 500 mg, about 500 mg and about 10 g, about 500 mg and about 5 g, about 500 mg and about 2.5 g, about 500 mg and about 1.4 g, about 500 mg and about 1 g, about 1 g and about 10 g, about 1 g and about 5 g, about 1 g and about 2.5 g, about 1 g and about 1.4 g, about 1.4 g and about 10 g, about 1.4 g and about 5 g, about 1.4 g and about 2.5 g, about 2.5 g and about 10 g, about 2.5 g and about 10 g, or about 5 g and about 10 g. In some embodiments, the chewing gum composition comprises between about 1.4 g and about 2.5 g of gum base.

In some embodiments, the gum base comprises as a weight percentage of the chewing gum core between about 5% to about 95%. In some embodiments, the gum base comprises as a weight percentage of the chewing gum core between about 5% and about 95%, about 5% and about 90%, about 5% and about 75%, about 5% and about 50%, about 5% and about 25%, about 5% and about 10%, about 10% and about 95%, about 10% and about 90%, about 10% and about 75%, about 10% and about 50%, about 10% and about 25%, about 25% and about 95%, about 25% and about 90%, about 25% and about 75%, about 25% and about 50%, about 25% and about 95%, about 25% and about 90%, about 25% and about 75%, about 25% and about 50%, about 50% and about 95%, about 50% and about 90%, about 50% and about 75%, about 75% and about 95%, about 75% and about 90%, or about 90% and about 95%.

In some embodiments, the water-insoluble gum base is a commercially available gum base.

In some embodiments, the gum base is a HEALTH IN GUM (Cafosa GUM SUA, Spain). In some embodiments, the gum base is HEALTH IN GUM PWD 01, HEALTH IN GUM PWD 03, or HEALTH IN GUM PWD 04. In some embodiments, the gum base in HEALTH IN GUM PWD 03. Properties of the HEALTH IN GUM gum bases are shown in TABLE 1.

TABLE 1

Properties of HIG gum bases.

| Property | HIG PWD 01 | HIG PWD 03 | HIG PWD 04 |
|---|---|---|---|
| Gum base content | 25% | 35% | 30% |
| Polyol content | Sorbitol/xylitol | Sorbitol/isomalt | Sorbitol/mannitol/xylitol |
| Water activity (Max) | 0.50% | 0.30% | 0.50% |
| Particle size (d50/µm) | 400 | 280 | 370 |

In some embodiments, the gum base is PG ALEX 13 T (Gum Base Co., Italy). The composition of PG ALEX 13 T is shown in TABLE 2.

TABLE 2

Properties of PG ALEX 13 T gum base.

| Ingredient | Weight Percentage |
|---|---|
| Gum Base | 76.8 |
| Isomalt | 17.3 |
| Talc (anticaking agent) | 5.8 |
| Antioxidant E321 | 0.036 |
| Soy Lecithin | 0.4 |

In some embodiments, the gum base comprises a HEALTH IN GUM gum base. In some embodiments, the gum base comprises a PG ALEX 13 T gum base. In some embodiments, the gum base comprises a HEALTH IN GUM and PG ALEX 13 T gum base.

In some embodiments, the gum base is a stiff gum base. A stiff gum base will help to clean the teeth during the chewing process and will help to control the release of the active ingredient. The stiffness of the gum base can be determined by measuring the Taber stiffness value. The Taber stiffness value is a measure of the chewing gum's resistance to bending. The longer the Taber stiffness value remains low, the longer the chewing gum remains flexible. The Taber stiffness can be measured using a Taber V-5 stiffness tester Model 150B (Taber Instrument Corporation, New York). See U.S. Pat. No. 5,223,282.

Active Ingredient

In some embodiments, the chewing gum composition comprises polyhexamethylene biguanide hydrochloride (polyhexanide, PHMB). In some embodiments, polyhexanide is the only antibacterially active ingredient in the chewing gum composition.

In some embodiments, the polyhexanide is any form of polyhexanide. Preparations of polyhexanide are polydisperse mixtures of polymeric biguanides, with a weighted average number of 12 repeating hexamethylene biguanide units. In some embodiments, the polyhexanide is a solid form. In some embodiments, the polyhexanide is in a solution. In some embodiments, the polyhexanide is a solid form with an average molecular weight in the range of 400 and 8000 g/mol. In some embodiments, the polyhexanide is a solid form with an average molecular weight in the range of 1600 and 3600 g/mol. In some embodiments, the polyhexanide is in a solution with an average molecular weight in the range of 400 and 8000 g/mol. In some embodiments, the polyhexanide is in a solution with an average molecular weight in the range of 1600 and 3600 g/mol.

In some embodiments, the polyhexanide solid is ground or micronized. In some embodiments, polyhexanide has a particle size between about 0.1 µm to about 500 µm. In some embodiments, polyhexanide has a particle size between about 0.1 µm and about 500 µm, about 0.1 µm and about 100 µm, about 0.1 µm and about 50 µm, about 0.1 µm and about 10 µm, about 0.1 µm and about 1 µm, about 0.1 µm and about 0.5 µm, about 0.5 µm and about 500 µm, about 0.5 µm and about 100 µm, about 0.5 µm and about 50 µm, about 0.5 µm and about 10 µm, about 0.5 µm and about 1 µm, about 1 µm and about 500 µm, about 1 µm and about 100 µm, about 1 µm and about 50 µm, about 1 µm and about 10 µm, about 10 µm and about 500 µm, about 10 µm and about 100 µm, about 10 µm and about 50 µm, about 50 µm and about 500 µm, about 50 µm and about 100 µm, or about 100 µm and about 500 µm. In some embodiments, polyhexanide has a particle size between about 1 µm and about 50 µm. In some embodiments, polyhexanide is reduced to a particle size of about 10 µm.

In some embodiments, the composition comprises polyhexanide only in the chewing gum core.

In some embodiments, the chewing gum core comprises by weight percentage between about 0.05% and about 10% polyhexanide. In some embodiments, the chewing gum core comprises polyhexanide by weight percentage between about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 10%, about 0.1% and about 8%, about 0.1% and about 6%, about 0.1% and about 4%, about 0.1% and about 2%, about 0.1% and about 1%, about 1% and about 10%, about 1% and about 8%, about 1% and about 6%, about 1% and about 4%, about 1% and about 2%, about 2% and about 10%, about 2% and about 8%, about 2% and about 6%, about 2% and about 4%, about 4% and about 10%, about 4% and about 8%, about 4% and about 6%, about 6% and about 10%, about 6% and about 8%, or about 8% and about 10%. In some embodiments, the chewing gum core comprises by weight percentage between about 4% and about 6% polyhexanide.

In some embodiments, the composition comprises polyhexanide in the chewing gum core and in at least one coating layer. In some embodiments, the composition comprises polyhexanide only in the coating layer.

In some embodiments, the composition comprises polyhexanide in one coating layer. In some embodiments, the composition comprises polyhexanide in two coating layers.

In some embodiments, the coating layer comprises by weight percentage between about 0.05% and about 10% polyhexanide. In some embodiments, the coating layer comprises polyhexanide by weight percentage between about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 10%, about 0.1% and about 8%, about 0.1% and about 6%, about 0.1% and about 4%, about 0.1% and about 2%, about 0.1% and about 1%, about 1% and about 10%, about 1% and about 8%, about 1% and about 6%, about 1% and about 4%, about 1% and about 2%, about 2% and about 10%, about 2% and about 8%, about 2% and about 6%, about 2% and about 4%, about 4% and about 10%, about 4% and about 8%, about 4% and about 6%, about 6% and about 10%, about 6% and about 8%, or about 8% and about 10%.

In some embodiments, the chewing gum composition comprises polyhexanide and at least one other antibacterially effective active ingredient.

In some embodiments, the at least one other antibacterially effective active ingredient is chlorhexidine digluconate, triclosan (2,4,4-trichloro-2-hydroxydiphenyl ether), hexylresorcinol, octenidine, an essential oil, or cetylpyridinium chloride. In some embodiments, the at least one other antibacterially effective active ingredient is chlorhexidine digluconate, triclosan (2,4,4-trichloro-2-hydroxydiphenyl ether), hexylresorcinol, octenidine, or cetylpyridinium chloride. In some embodiments, the at least one other antibacterially effective active ingredient is chlorhexidine digluconate.

In some embodiments, the at least one other antibacterially effective active ingredient is in the core. In some embodiments, the at least one other antibacterially effective active ingredient is in the coating layer.

In some embodiments, polyhexanide is in the core and the at least one other antibacterially effective active ingredient is also in the core. In some embodiments, polyhexanide is in the core and the at least one other antibacterially effective active ingredient is in the coating layer. In some embodiments, polyhexanide is in the coating layer and the at least one other antibacterially effective active ingredient is in the core. In some embodiments, polyhexanide is in the coating layer and the at least one other antibacterially effective active ingredient is also in the coating layer.

Other Additives

In some embodiments, the chewing gum composition comprises at least one additive selected from the group consisting of a stabilizer, a preservative, an antioxidant, a softener, a thickening agent, an emulsifier, a lubricant, a sweetener, a flavor, an aromatic, a filler, an enhancer, a coloring additive, a vitamin, a mineral, a fluoride, a cleaning abrasive, and a tooth whitening agent.

In some embodiments, the chewing gum composition comprises an antioxidant. In some embodiments, the chewing gum composition comprises an antioxidant in the gum base, the chewing gum core, or the coating layer. In some embodiments, the chewing gum composition comprises an antioxidant in the gum base. Antioxidants can improve the shelf-life and storage of the gum base, finished gum or their respective components, including fats and flavor oils.

In some embodiments, the antioxidant suitable for use in the gum base or chewing gum core includes butylated hydroxyanisole (BHA), butylated hydroxytoluene (BHT), beta-carotenes, tocopherols, vitamin C, propyl gallate, or mixtures thereof. In some embodiments, the antioxidant is BHA, BHT, tocopherol, or mixtures thereof.

In some embodiments, the chewing gum core comprises by weight percentage between about 0.001% and about 0.10% of an antioxidant. In some embodiments, the chewing gum core comprises an antioxidant by weight percentage between about 0.001% and about 0.10%, about 0.001% and about 0.05%, about 0.001% and about 0.01%, about 0.001% and about 0.005%, about 0.005% and about 0.10%, about 0.005% and about 0.05%, 0.005% and about 0.01%, about 0.01% and about 0.10%, about 0.01% and about 0.05%, and about 0.05% and about 0.10%. In some embodiments, the chewing gum core comprises by weight percentage between about 0.001% and about 0.005% of an antioxidant.

In some embodiments, the chewing gum composition comprises a fluoride. In some embodiments, the chewing gum composition comprises a fluoride in the chewing gum core. In some embodiments, the fluoride is a fluoride salt selected from the group consisting of sodium fluoride, potassium fluoride, stannous fluoride, potassium stannous fluoride, lithium fluoride, ammonium fluoride, tin fluoride, indium fluoride, zirconium fluoride, copper fluoride, nickel fluoride, palladium fluoride, zinc fluoride, ammonium fluoride, stannous chloroflouride, sodium monofluorophosphate, ammonium monofluorophosphate, aluminum monofluorophosphate, and mixtures thereof. In some embodiments, the chewing gum composition comprises sodium fluoride.

In some embodiments, the chewing gum core comprises by weight percentage between about 0.001% and about 0.10% of a fluoride salt. In some embodiments, the chewing gum core comprises a fluoride salt by weight percentage between about 0.001% and about 0.10%, about 0.001% and about 0.05%, about 0.001% and about 0.01%, about 0.001% and about 0.005%, about 0.005% and about 0.10%, about 0.005% and about 0.05%, 0.005% and about 0.01%, about 0.01% and about 0.10%, about 0.01% and about 0.05%, and about 0.05% and about 0.10%. In some embodiments, the chewing gum core comprises by weight percentage between about 0.001% and about 0.01% of sodium fluoride.

In some embodiments, the fluoride in the chewing gum core is in an amount that is not antibacterially effective.

In some embodiments, the chewing gum composition comprises at least one sweetener. In some embodiments, the sweetener is a sugar sweetener. In some embodiments, the sweetener is a sugar-free sweetener. In some embodiments, the sweetener also fulfills the role of a bulking agent in the chewing gum composition.

In some embodiments, the chewing gum composition comprises at least one sugar sweetener. In some embodiments, the at least one sugar sweetener is selected from the group consisting of sucrose, dextrose, maltose, dextrin, inverted sugar syrup, fructose, levulose, galactose, and corn syrup solids.

In some embodiments, the chewing gum composition comprises at least one sugar-free sweetener. In some embodiments, the chewing gum composition comprises at least one sugar-free sweetener selected from the group consisting of saccharin, aspartame, acesulfame potassium, sucralose, alitame, sorbitol, mannitol, maltitol, xylitol, isomalt, erythritol, lactitol, neotame, advantame, stevia, and hydrogenated starch hydrolysate.

In some embodiments, the chewing gum composition comprises at least one sweetener in the chewing gum core. In some embodiments, the chewing gum composition comprises 1, 2, 3, 4, or 5 sweeteners in the chewing gum core. In some embodiments, the chewing gum composition comprises 4 sweeteners in the chewing gum core.

In some embodiments, the chewing gum core comprises by weight percentage between about 0.01% and about 50% of at least one sweetener. In some embodiments, the chewing gum core comprises at least one sweetener by weight percentage between about 0.01% and about 50%, about 0.01% and about 10%, about 0.01% and about 8%, about 0.01% and about 6%, about 0.01% and about 4%, about 0.01% and about 2%, about 0.01% and about 1%, about 0.05% and about 50%, 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 50%, about 0.1% and about 10%, about 0.1% and about 8%, about 0.1% and about 6%, about 0.1% and about 4%, about 0.1% and about 2%, about 0.1% and about 1%, about 1% and about 50%, about 1% and about 10%, about 1% and about 8%, about 1% and about 6%, about 1% and about 4%, about 1% and about 2%, about 2% and about 50%, about 2% and about 10%, about 2% and about 8%, about 2% and about 6%, about 2% and about 4%, about 4% and about 50%, about 4% and about 10%, about 4% and about 8%, about 4% and about 6%, about 6% and about 50%, about 6% and about 10%, about 6% and about 8%, about 8% and about 50%, about 8% and about 10%, or about 10% and about 50%. In some embodiments, the chewing gum core comprises by weight percentage between about 4% and about 6% of at least one sweetener.

In some embodiments, the chewing gum composition comprises at least one flavor. In some embodiments, the at least one flavor comprises an essential oil, a synthetic flavor, or mixtures thereof. In some embodiments, the at least one flavor is a citrus, a fruit, peppermint, spearmint, wintergreen, cinnamon, cocoa, vanilla, licorice, menthol, *eucalyptus*, anise, or almond. In some embodiments, the at least one flavor is spearmint.

In some embodiments, the chewing gum composition comprises 1, 2, 3, 4, or 5 flavors in the chewing gum core. In some embodiments, the chewing gum composition comprises 1 flavor in the chewing gum core.

In some embodiments, the chewing gum core comprises by weight percentage between about 0.05% and about 10% of at least one flavor. In some embodiments, the chewing gum core optionally comprises at least one flavor by weight percentage up to about 10%. In some embodiments, the chewing gum core comprises at least one flavor by weight percentage between about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 10%, about 0.1% and about 8%, about 0.1% and about 6%, about 0.1% and about 4%, about 0.1% and about 2%, about 0.1% and about 1%, about 1% and about 10%, about 1% and about 8%, about 1% and about 6%, about 1% and about 4%, about 1% and about 2%, about 2% and about 10%, about 2% and about 8%, about 2% and about 6%, about 2% and about 4%, about 4% and about 10%, about 4% and about 8%, about 4% and about 6%, about 6% and about 10%, about 6% and about 8%, or about 8% and about 10%. In some embodiments, the chewing gum core comprises by weight percentage between about 4% and about 6% of at least one flavor.

In some embodiments, the chewing gum composition comprises at least one coloring additive. In some embodiments, the coloring additive is a dye approved as a food additive. In some embodiments, the coloring additive is a commercial available coloring additive. In some embodiments, the coloring additive is Sensipearl Intence Silver.

In some embodiments, the chewing gum composition comprises at least one coloring additive in the chewing gum core. In some embodiments, the chewing gum composition does not comprise a coloring additive in the chewing gum core.

In some embodiments, the chewing gum composition comprises at least one filler. In some embodiments, the filler increases flowability and prevents clumping of the particles. In some embodiments, the filler is calcium carbonate, magnesium carbonate, magnesium stearate, magnesium silicate, aluminum silicate, calcium phosphate, talc, dicalcium phosphate, or sodium carbonate.

In some embodiments, the chewing gum composition comprises 1, 2, 3, 4, or 5 fillers in the chewing gum core. In some embodiments, the chewing gum composition comprises 3 fillers in the chewing gum core.

In some embodiments, the chewing gum core optionally comprises by weight percentage up to about 40% of at least one filler. In some embodiments, the chewing gum core comprises by weight percentage between about 0.05% and about 40% of at least one filler. In some embodiments, the chewing gum core comprises at least one filler by weight percentage between about 0.05% and about 40%, 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 40%, about 0.1% and about 10%, about 0.1% and about 8%, about 0.1% and about 6%, about 0.1% and about 4%, about 0.1% and about 2%, about 0.1% and about 1%, about 1% and about 40%, about 1% and about 10%, about 1% and about 8%, about 1% and about 6%, about 1% and about 4%, about 1% and about 2%, about 2% and about 2% and about 40%, about 2% and about 10%, about 2% and about 8%, about 2% and about 6%, about 2% and about 4%, about 4% and about 40%, about 4% and about 10%, about 4% and about 8%, about 4% and about 6%, about 6% and about 40%, about 6% and about 10%, about 6% and about 8%, about 8% and about 40%, about 8% and about 10%, or about 10% and about 40%. In some embodiments, the chewing gum core comprises by weight percentage between about 4% and about 6% of at least one filler.

In some embodiments, the chewing gum composition comprises at least one 1, 2, 3, 4, or 5 fillers in the coating layer. In some embodiments, the chewing gum composition comprises 2 fillers in the coating layer.

In some embodiments, the coating layer comprises by weight percentage between about 0.05% and about 10% of at least one filler. In some embodiments, the chewing gum core comprises at least one filler by weight percentage between about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 10%, about 0.1% and about 8%, about 0.1% and about 6%, about 0.1% and about 4%, about 0.1% and about 2%, about 0.1% and about 1%, about 1% and about 10%, about 1% and about 8%, about 1% and about 6%, about 1% and about 4%, about 1% and about 2%, about 2% and about 10%, about 2% and about 8%, about 2% and about 6%, about 2% and about 4%, about 4% and about 10%, about 4% and about 8%, about 4% and about 6%, about 6% and about 10%, about 6% and about 8%, or about 8% and about 10%. In some embodiments, the coating layer comprises by weight percentage between about 4% and about 6% of at least one filler.

Softeners can be added to the chewing gum composition in order to optimize the chewability and mouth feel of the gum. Softeners, also known in the art as plasticizers or plasticizing agents, include glycerin, glycerol monoacetate, stearic acid, cocoa butter, lecithin, and soy lecithin.

In some embodiments, the chewing gum core optionally comprises by weight percentage up to about 15% of at least one softener. In some embodiments, the chewing gum core comprises by weight percentage between about 0.05% and about 15% of at least one softener. In some embodiments, the chewing gum core comprises at least one softener by weight percentage between about 0.05% and about 15%, about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 15%, about 0.1% and about 10%, about 0.1% and about 8%, about 0.1% and about 6%, about 0.1% and about 4%, about 0.1% and about 2%, about 0.1% and about 1%, about 1% and about 15%, about 1% and about 10%, about 1% and about 8%, about 1% and about 6%, about 1% and about 4%, about 1% and about 2%, about 2% and about 15%, about 2% and about 10%, about 2% and about 8%, about 2% and about 6%, about 2% and about 4%, about 4% and about 15%, about 4% and about 10%, about 4% and about 8%, about 4% and about 6%, about 6% and about 15%, about 6% and about 10%, about 6% and about 8%, about 8% and about 15%, about 8% and about 10%, or about 10% and about 15%. In some embodiments, the chewing gum core comprises by weight percentage between about 4% and about 6% of at least one softener.

In some embodiments, the chewing gum core comprises at least one emulsifier. In some embodiments, the at least one emulsifier is lecithin or glycerol monostearate.

In some embodiments, the chewing gum core optionally comprises by weight percentage up to about 15% of at least one emulsifier. In some embodiments, the chewing gum core comprises by weight percentage between about 0.05% and about 15% of at least one emulsifier. In some embodiments, the chewing gum core comprises at least one softener by weight percentage between about 0.05% and about 15%, about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 15%, about 0.1% and about 10%, about 0.1% and about 8%, about 0.1% and about 6%, about 0.1% and about 4%, about 0.1% and about 2%, about 0.1% and about 1%, about 1% and about 15%, about 1% and about 10%, about 1% and about 8%, about 1% and about 6%, about 1% and about 4%, about 1% and about 2%, about 2% and about 15%, about 2% and about 10%, about 2% and about 8%, about 2% and about 6%, about 2% and about 4%, about 4% and about 15%, about 4% and about 10%, about 4% and about 8%, about 4% and about 6%, about 6% and about 15%, about 6% and about 10%, about 6% and about 8%, about 8% and about 15%, about 8% and about 10%, or about 10% and about 15%. In some embodiments, the chewing gum core comprises by weight percentage between about 4% and about 6% of at least one emulsifier.

In some embodiments, the chewing gum core optionally comprises at least one fat or wax. In some embodiments, the fat or wax is a microcrystalline wax, a paraffin wax, or a bee wax.

In some embodiments, the chewing gum core optionally comprises by weight percentage up to about 15% of at least one fat or wax. In some embodiments, the chewing gum core comprises by weight percentage between about 0.05% and about 15% of at least one fat or wax. In some embodiments, the chewing gum core comprises at least one fat or wax by weight percentage between about 0.05% and about 15%, about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 15%, about 0.1% and about 10%, about 0.1% and about 8%, about 0.1% and about 6%, about 0.1% and about 4%, about 0.1% and about 2%, about 0.1% and about 1%, about 1% and about 15%, about 1% and about 100%, about 1% and about 8%, about 1% and about 6%, about 1% and about 4%, about 1% and about 2%, about 2% and about 15%, about 2% and about 10%, about 2% and about 8%, about 2% and about 6%, about 2% and about 4%, about 4% and about 15%, about 4% and about 10%, about 4% and about 8%, about 4% and about 6%, about 6% and about 15%, about 6% and about 10%, about 6% and about 8%, about 8% and about 15%, about 8% and about 10%, or about 10% and about 15%. In some embodiments, the chewing gum core comprises by weight percentage between about 4% and about 6% of at least one fat or wax.

In some embodiments, the chewing gum core comprises microgranules. In some embodiments, the microgranules are water-soluble. In some embodiments, the microgranules have a mean particle size between about 100 μm and about 2000 μm. In some embodiments, the microgranules enhance the cleaning effect of the chewing gum composition. In some embodiments, the microgranules comprise a polyalcohol, a hydrocolloid, a flavor, a dye, a sweetener, an excipient, or combinations thereof.

Coating Layer

In some embodiments, the chewing gum composition comprises at least one coating layer. In some embodiments, the chewing gum composition comprises between 1 and 10 coating layers. In some embodiments, the chewing gum composition comprises between 1 and 10, 1 and 8, 1 and 6, 1 and 4, 1 and 2, 2 and 10, 2 and 8, 2 and 6, 2 and 4, 4 and 10, 4 and 8, 4 and 6, 6 and 10, 6 and 8, or 8 and 10 coating layers. In some embodiments, the chewing gum composition comprises 1, 2, 3, 4, or 5 coating layers.

In some embodiments, the chewing gum composition comprises at least one sweetener in the coating layer. In some embodiments, the sweetener is a sugar sweetener, a sugar-free sweetener, or combinations thereof. In some embodiments, the chewing gum composition comprises 1, 2, 3, 4, or 5 sweeteners in the coating layer. In some embodiments, the chewing gum composition comprises 3 sweeteners in the coating layer.

In some embodiments, the at least one sweetener in the coating layer is a sugar-free sweetener selected from the group consisting of sucrose, dextrose, maltose, dextrin, inverted sugar syrup, fructose, levulose, galactose, and corn syrup solids.

In some embodiments, the at least one sweetener in the coating layer is a sugar-free sweetener selected from the group consisting of saccharin, aspartame, acesulfame potassium, sucralose, alitame, sorbitol, mannitol, maltitol, xylitol, isomalt, erythritol, lactitol, neotame, advantame, stevia, and hydrogenated starch hydrolysate.

In some embodiments, the chewing gum composition comprises at least one sugar-free sweetener in the coating layer. In some embodiments, the coating layer comprises 3 sugar-free sweeteners. In some embodiments, the coating layer comprises 2 sugar-free sweeteners. In some embodiments, the coating layer comprises 1 sugar-free sweetener.

In some embodiments, the coating layer comprises 3 sugar sweeteners. In some embodiments, the coating layer comprises 2 sugar sweeteners. In some embodiments, the coating layer comprises 1 sugar sweetener.

In some embodiments, the coating layer comprises by weight percentage between about 10% and about 95% of at least one sweetener. In some embodiments, the chewing gum core comprises at least one sweetener by weight percentage between about 10% and about 95%, about 10% and about 90%, about 10% and about 80%, about 10% and about 60%, about 10% and about 40%, about 10% and about 20%, about 20% and about 95%, about 20% and about 90%, about 20% and about 80%, about 20% and about 60%, about 20% and about 40%, about 40% and about 95%, about 40% and about 90%, about 40% and about 80%, about 40% and about 60%, about 60% and about 95%, about 60% and about 90%, about 60% and about 80%, about 80% and about 95%, about 80% and about 90%, or about 90% and about 95%. In some embodiments, the coating layer comprises by weight percentage between about 40% and about 60% of at least one sweetener.

In some embodiments, the chewing gum composition comprises at least one 1, 2, 3, 4, or 5 flavors in the coating layer. In some embodiments, the chewing gum composition comprises 2 flavors in the coating layer. In some embodiments, the at least one flavor in the coating layer comprises an essential oil, a synthetic flavor, or mixtures thereof. In some embodiments, the at least one flavor is a citrus, a fruit, peppermint, spearmint, wintergreen, cinnamon, cocoa, vanilla, licorice, menthol, *eucalyptus*, anise, or almond. In some embodiments, the at least one flavor is spearmint.

In some embodiments, the coating layer optionally comprises by weight percentage up to about 20% of at least one flavor. In some embodiments, the coating layer comprises by weight percentage between about 0.05% and about 20% of at least one flavor. In some embodiments, the chewing gum core comprises at least one flavor by weight percentage between about 0.05% and about 20%, about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 20%, about 0.1% and about 10%, about 0.1% and about 8%, about 0.1% and about 6%, about 0.1% and about 4%, about 0.1% and about 2%, about 0.1% and about 1%, about 1% and about 20%, about 1% and about 10%, about 1% and about 8%, about 1% and about 6%, about 1% and about 4%, about 1% and about 2%, about 2% and about 20%, about 2% and about 10%, about 2% and about 8%, about 2% and about 6%, about 2% and about 4%, about 4% and about 20%, about 4% and about 10%, about 4% and about 8%, about 4% and about 6%, about 6% and about 20%, about 6% and about 10%, about 6% and about 8%, about 8% and about 20%, about 8% and about 10%, or about 10% and about 20%. In some embodiments, the coating layer comprises by weight percentage between about 4% and about 6% of at least one flavor.

In some embodiments, the flavor is in the form of microgranules.

In some embodiments, the coating layer comprises microgranules. In some embodiments, the microgranules comprise a polyalcohol, a hydrocolloid, a flavor, a dye, a sweetener, an excipient, or combinations thereof. In some embodiments, the microgranules are menthol microgranules. In some embodiments, the menthol microgranules comprise menthol, sorbitol, maize maltodextrin, modified waxy maize starch, methyl cellulose, and Brilliant Blue FCF.

In some embodiments, the chewing gum composition comprises at least one coloring additive in the coating layer.

In some embodiments, the chewing gum composition comprises at least one 1, 2, 3, 4, or 5 fillers in the coating layer. In some embodiments, the chewing gum composition comprises 2 fillers in the coating layer. In some embodiments, the filler is calcium carbonate, magnesium carbonate, magnesium stearate, magnesium silicate, aluminum silicate, calcium phosphate, talc, dicalcium phosphate, silicon dioxide, or sodium carbonate.

In some embodiments, the coating layer comprises by weight percentage between about 0.05% and about 10% of at least one filler. In some embodiments, the chewing gum core comprises at least one filler by weight percentage between about 0.05% and about 10%, about 0.05% and about 8%, about 0.05% and about 6%, about 0.05% and about 4%, about 0.05% and about 2%, about 0.05% and about 1%, about 0.05% and about 0.1%, about 0.1% and about 10%, about 0.1% and about 8%, about 0.1% and about 6%, about 0.1% and about 4%, about 0.10% and about 2%, about 0.1% and about 1%, about 1% and about 10%, about 1% and about 8%, about 1% and about 6%, about 1% and about 4%, about 1% and about 2%, about 2% and about 10%, about 2% and about 8%, about 2% and about 6%, about 2% and about 4%, about 4% and about 10%, about 4% and about 8%, about 4% and about 6%, about 6% and about 10%, about 6% and about 8%, or about 8% and about 10%. In some embodiments, the coating layer comprises by weight percentage between about 4% and about 6% of at least one filler.

Manufacture of the Chewing Gum Composition

In some embodiments, the chewing gum core is manufactured by sequentially adding the various chewing gum ingredients to a commercially available mixer known in the art. After the ingredients have been thoroughly mixed, the gum core is discharged from the mixer and shaped into the desired form. In some embodiments, the final product shape is a stick, a tablet, a chunk, a pellet, or a ball.

In some embodiments, the chewing gum core is mixed at a temperature between about 0° C. and about 40° C. In some embodiments, the chewing gum core is mixed at a temperature between about 0° C. and about 40° C., about 0° C. and about 30° C., about 0° C. and about 25° C., about 0° C. and about 20° C., about 20° C. and about 40° C., about 20° C. and about 30° C., about 20° C. and about 25° C., about 25° C. and about 40° C., about 25° C. and about 30° C., or about 30° C. and about 40° C. In some embodiments, the chewing gum core is mixed at a temperature between about 20° C. and about 25° C.

In some embodiments, the chewing gum core is shaped into the desired form by rolling into sheets and cutting into sticks. In some embodiments, the chewing gum core is shaped into the desired form by extruding into chunks. In some embodiments, the chewing gum core is shaped into the desired form by casting into pellets. In some embodiments, the chewing gum core is shaped into the desired form using a tablet press to produce tablets.

A tablet press comprises a die and a punch and the basic principle of compression applies wherein the die is filled with powder and compressed by the punch being lowered under pressure and maintained on the powder for a period of time (dwell time) to form the tablet which is then ejected. Many shapes and sizes of tablet can be produced by varying the shape of the die and punch. In some embodiments, the tablet is circular, a briquette, or a pillow.

In some embodiments, the powder is compressed at a compression force to control the release dynamics of the tablet. In some embodiments, the powder is subjected to a compression force between about 1 $kN/cm^2$ and about 50 $kN/cm^2$. In some embodiments, the powder is subjected to a compression force between about 1 $kN/cm^2$ and about 50 $kN/cm^2$, about 1 $kN/cm^2$ and about 30 $kN/cm^2$, about 1 $kN/cm^2$ and about 20 $kN/cm^2$, about 1 $kN/cm^2$ and about 10 $kN/cm^2$, about 1 $kN/cm^2$ and about 5 $kN/cm^2$, about 5 $kN/cm^2$ and about 50 $kN/cm^2$, about 5 $kN/cm^2$ and about 30 $kN/cm^2$, about 5 $kN/cm^2$ and about 20 $kN/cm^2$, about 5 $kN/cm^2$ and about 10 $kN/cm^2$, about 10 $kN/cm^2$ and about 50 $kN/cm^2$, about 10 $kN/cm^2$ and about 30 $kN/cm^2$, about 10 $kN/cm^2$ and about 20 $kN/cm^2$, about 20 $kN/cm^2$ and about 50 $kN/cm^2$, about 20 $kN/cm^2$ and about 30 $kN/cm^2$, or about 30 $kN/cm^2$ and about 50 $kN/cm^2$. In some embodiments, the powder is subjected to a compression force between about 10 $kN/cm^2$ and about 30 $kN/cm^2$. In some embodiments, the powder is subjected to a compression force of about 20 $kN/cm^2$. In some embodiments, the powder is subjected to a compression force of between about 20 $kN/cm^2$ and about 50 $kN/cm^2$, about 24 $kN/cm^2$ and about 40 $kN/cm^2$, or about 24 $kN/cm^2$ and about 35 $kN/cm^2$.

When using a press with more than one punch (for example a tablet press with two punches) for preparing the chewing gum, the compression force refers to the average compression force of the punches.

In some embodiments, a coating layer is added to a chewing gum core by a technique known to those of skill in the art. In some embodiments, the coating layer is added to the chewing gum core to add crispiness, to enhance taste, to protect the gum during storage, to stimulate saliva flow, to produce a cleaning effect, to control the release dynamics of the active ingredient, or to tone down a bad or irritating taste of the gum core.

In some embodiments, the coating layer comprises microgranules.

In some embodiments, the coating layer is applied by sugar coating, film coating, press coating, or melt coating.

Sugar coating involves the deposition, either by a manual or a spray method, of a sugar coating onto the core. In some embodiments, the sugar coating is deposited using a panning technique. In some embodiments, the sugar coating is deposited using a spray method.

Application of a sugar coating typically involves 5 steps: sealing, subcoating, grossing, color coating, and polishing. Sealing is the application of a polymer-based coating to the surface of the chewing gum core. Subcoating is the means to round off the chewing gum core edges and build up the core weight. Subcoating formulations contain high levels of fillers (including sweeteners such as xylitol and mannitol). Grossing can be achieved by application of a coating syrup (such as sucralose), which can contain titanium dioxide. Color coating can be achieved by the use of a color additive dissolved in the coating syrup. Finally, because the freshly coated chewing gum compositions are dull, it is necessary to polish them to achieve a glossy finish.

Film coating involves the deposition, usually by a spray method of a thin film of polymer and other ingredients onto the core.

Press coating involves the compaction of granular material around an already manufactured core.

Controlled Release of the Active Ingredient

In some embodiments, the polyhexanide is released by controlled release from the chewing gum composition. In some embodiments, the controlled release of polyhexanide from the chewing gum composition is dependent on the following: (1) the size of the gum base; (2) the elasticity and plasticity of the gum base/water-insoluble content of the chewing gum; (3) the particle size of the active ingredient (i.e., polyhexanide); (4) the compression force applied during manufacturing of the chewing gum composition; (5) the chewing rate; and (6) the use of a lipophilic substance (e.g., elastomers, softeners (plasticizers), emulsifiers, fats or waxes, and fillers) in the chewing gum composition. In some embodiments, the release profile is optimized for average chewing behavior (60 chews/minute), wherein mere sucking of the chewing gum or very fast chewing may result in reduced or increased polyhexanide release, respectively. In some embodiments, a desirable controlled release can be achieved with a chewing gum composition having a total core weight of between 1.4 g and 2.5 g and a weight of polyhexanide in the core between about 2 mg and about 50 mg, wherein the chewing gum composition is prepared by using a compression force of between about 1 kN/cm$^2$ to about 50 kN/cm$^2$, wherein the chewing gum composition comprises the lipophilic substance soy lecithin, and wherein the particle size of the polyhexanide is between about 1 μm and about 500 μm. In some embodiments, a desirable controlled release can be achieved with a chewing gum composition having a total core weight of between 1.4 g and 2.5 g and a weight of polyhexanide in the core between about 2 mg and about 50 mg, wherein the chewing gum composition is prepared by using a compression force of between about 1 kN/cm$^2$ to about 50 kN/cm$^2$, wherein the chewing gum composition optionally comprises the lipophilic substance soy lecithin and/or optionally comprises at least 15% elastomers by weight of the gum base and/or optionally comprises at least 47% plasticizers by weight of the gum base, wherein the particle size of the polyhexanide is between about 1 μm and about 500 μm, wherein the release of polyhexanide is sustained over a desired period of time, and wherein optionally between about 5% and about 30% of the polyhexanide is released in the first 2 minutes from initiation of a chewing process and between about 75% and about 100% of the polyhexanide is released in the first 15 minutes from initiation of a chewing process. The release of polyhexanide is thereby sustained over a desired period of time.

In some embodiments, between about 5% and about 30% of the polyhexanide is released within 2 minutes from initiation of a chewing process and between about 75% and about 100% of the polyhexanide is released within 15 minutes from initiation of a chewing process. This release may provide very good results since it provides the desired release over the usual chewing time of a user and the user does not have to comply with instructions for use that differ from those for normal use of a chewing gum without an active ingredient. The additional use of a coating layer (e.g., a sugar coating layer) can further enhance the efficacy because the coating layer readily dissolves in the mouth and stimulates saliva production which is believed to contribute to the release of the polyhexanide from the chewing gum core.

In some embodiments, the polyhexanide is released over a period of 5, 10, 20, 30, 40, 50, or 60 minutes. In some embodiments, chewing the chewing gum composition results in a slow release of the polyhexanide over a period of between about 1 minute and about 60 minutes, about 1 minute and about 30 minutes, about 1 minute and about 15 minutes, about 1 minute and about 10 minutes, about 2 minutes and about 60 minutes, about 2 minutes and about 30 minutes, about 2 minutes and about 15 minutes, about 2 minutes and about 10 minutes, about 5 minutes and about 60 minutes, about 5 minutes and about 30 minutes, about 5 minutes and about 15 minutes, or about 5 minutes and about 10 minutes.

Release of polyhexanide from the chewing gum composition can be measured using a chewing machine as described in Chewing Apparatus DRT1-3 AB FIA Odarslövs mölla.

In some embodiments, 1 chewing gum composition is chewed singly. In some embodiments, between 2 and 10 chewing gum compositions are chewed simultaneously. In some embodiments, between 2 and 10, 2 and 8, 2 and 6, 2 and 4, 4 and 10, 4 and 8, 4 and 6, 6 and 10, 6 and 8, or 8 and 10 chewing gum compositions are chewed simultaneously. In some embodiments, 2, 3, 4, 5, 6, 7, 8, 9, or 10 chewing gum compositions are chewed simultaneously. In some embodiments, wherein between 2 and 10 chewing gum compositions are chewed simultaneously, the size of each chewing gum composition is the same. In some embodiments, wherein between 2 and 10 chewing gum compositions are chewed simultaneously, the size of each chewing gum composition is different.

In some embodiments, between about 5% and about 30% of the polyhexanide is released in the first 2 minutes from initiation of a chewing process. In some embodiments, between about 5% and about 30%, about 5% and about 25%, about 5% and about 20%, about 5% and about 15%, about 5% and about 10%, about 10% and about 30%, about 10% and about 25%, about 10% and about 20%, about 10% and about 15%, about 15% and about 30%, about 15% and about 25%, about 15% and about 20%, about 20% and about 30%, about 20% and about 25%, or about 25% and about 30% of the polyhexanide is released in the first 2 minutes from initiation of a chewing process.

In some embodiments, between about 15% and about 60% of the polyhexanide is released in the first 5 minutes from initiation of a chewing process. In some embodiments, between about 15% and about 60%, about 15% and about 55%, about 15% and about 50%, about 15% and about 45%, about 15% and about 40%, about 20% and about 60%, about 20% and about 55%, about 20% and about 50%, about 20% and about 45%, about 25% and about 60%, about 25% and about 55%, about 25% and about 50%, about 30% and about 60%, about 30% and about 55%, or about 35% and about 60% of the polyhexanide is released in the first 5 minutes from initiation of a chewing process.

In some embodiments, between about 75% and about 100% of the polyhexanide is released in the first 15 minutes from initiation of a chewing process. In some embodiments, between about 75% and about 100%, about 75% and about 95%, about 75% and about 90%, about 75% and about 85%, about 75% and about 80%, about 80% and about 100%, about 80% and about 95%, about 80% and about 90%, about 80% and about 85%, about 85% and about 100%, about 85% and about 95%, about 85% and about 90%, about 90% and about 100%, about 90% and about 95%, or about 95% and about 1000% of the polyhexanide is released in the first 15 minutes from initiation of a chewing process.

In some embodiments, less than 50% of the polyhexanide is released in the first 2 minutes from initiation of a chewing process. In some embodiments, less than 30% of the polyhexanide is released in the first 2 minutes from initiation of a chewing process. In some embodiments, less than 50%, 45%, 40%, 35%, 30%, 25%, 20%, 15%, or 10% of the polyhexanide is released in the first 2 minutes from initiation of a chewing process. In some embodiments, less than 25% of the polyhexanide is released in the first 2 minutes from initiation of a chewing process.

In some embodiments, less than 50% of the total polyhexanide content is released within the first 4 minutes from initiation of a chewing process. In some embodiments, less than 50% of the polyhexanide is released within the first 4 minutes from initiation of a chewing process and greater than 75% of the total polyhexanide content is released within the first 15 minutes from initiation of a chewing process.

In some embodiments, greater than 75% of the polyhexanide is released within 15 minutes from initiation of a chewing process. In some embodiments, greater than 75%, 80%, 85%, 90%, or 95% of the polyhexanide is released within 15 minutes from initiation of a chewing process.

In addition to the various embodiments described above, the present disclosure includes the following specific embodiments numbered E1 through E42. This list of embodiments is presented as an exemplary list and the application is not limited to these embodiments.

E1. A chewing gum composition comprising polyhexanide, wherein the chewing gum composition comprises a chewing gum core, and wherein the chewing gum core comprises between about 0.05% and about 10% polyhexanide by weight, wherein the weight percentage of the total chewing gum core that is water-insoluble is between about 15% and about 60%.

E2. The chewing gum composition of E1, wherein the chewing gum core comprises between about 0.01% and about 5% polyhexanide by weight.

E3. The chewing gum composition of E1 or E2, wherein the chewing gum core was formed using a compression force of between about 1 kN/cm$^2$ and about 50 kN/cm$^2$.

E4. The chewing gum composition of any one of E1-E3, wherein the chewing gum core was formed using a compression force of between about 5 kN/cm$^2$ and about 50 kN/cm$^2$.

E5. The chewing gum composition of any one of E1-E4, wherein the chewing gum core was formed using a compression force of between about 20 kN/cm$^2$ and about 50 kN/cm$^2$.

E6. The chewing gum composition of any one of E1-E5, further comprising a fluoride salt.

E7. The chewing gum composition of E6, wherein the fluoride salt is selected from the group consisting of sodium fluoride, potassium fluoride, stannous fluoride, potassium stannous fluoride, lithium fluoride, ammonium fluoride, tin fluoride, indium fluoride, zirconium fluoride, copper fluoride, nickel fluoride, palladium fluoride, zinc fluoride, ammonium fluoride, stannous chloroflouride, sodium monofluorophosphate, ammonium monofluorophosphate, aluminum monofluorophosphate, and mixtures thereof.

E8. The chewing gum composition of E6 or E7, wherein the chewing gum core comprises between about 0.001% and about 0.10% of the fluoride salt by weight.

E9. The chewing gum composition of any one of E1-E8, further comprising at least one sweetener.

E10. The chewing gum composition of E9, wherein the at least one sweetener is selected from the group consisting of saccharin, aspartame, acesulfame potassium, sucralose, alitame, sorbitol, mannitol, maltitol, xylitol, isomalt, erythritol, lactitol, neotame, advantame, stevia, and hydrogenated starch hydrolysate.

E11. The chewing gum composition of E9 or E10, wherein the chewing gum core comprises between about 0.05% to about 10% of the at least one sweetener by weight.

E12. The chewing gum composition of any one of E1-E11, further comprising at least one flavor.

E13. The chewing gum composition of E12, wherein the at least one flavor is selected from the group consisting of a citrus, a fruit, peppermint, spearmint, wintergreen, cinnamon, cocoa, vanilla, licorice, menthol, *eucalyptus*, anise, and almond.

E14. The chewing gum composition of E12 or E13, wherein the chewing gum core comprises between about 0.05% to about 10% of the at least one flavor by weight.

E15. The chewing gum composition of any one of E1-E14, further comprising at least one filler.

E16. The chewing gum composition of E15, wherein the at least one filler is selected from the group consisting of calcium carbonate, magnesium carbonate, magnesium stearate, magnesium silicate, aluminum silicate, calcium phosphate, talc, dicalcium phosphate, and sodium carbonate.

E17. The chewing gum composition of E15 or E16, wherein the chewing gum core comprises between about 0.05% to about 10% of the at least one filler by weight.

E18. The chewing gum composition of any one of E1-E17, further comprising at least one gum base.

E19. The chewing gum composition of E18, wherein the at least one gum base is a synthetic gum base or a natural gum base.

E20. The chewing gum composition of E18 or E19, wherein the chewing gum core comprises between about 5% to about 95% of the at least one gum base by weight.

E21. The chewing gum composition of any one of E18-E20, wherein the at least one gum base is a synthetic gum base selected from the group consisting of polyvinyl acetate, polyvinyl laurate, polyvinyl alcohol, polyvinyl pyrrolidone, polyisobutylene, butyl rubber, and styrene butadiene rubber.

E22. The chewing gum composition of any one of E18-E21, wherein the at least one gum base is HEALTH IN GUM PWD 03 and PG ALEX 13 T.

E23. The chewing gum composition of any one of E1-E22, further comprising a fluoride salt, at least one sweetener, at least one flavor, at least one filler, and at least one gum base.

E24. The chewing gum composition of any one of E1-E23, wherein less than 50% of the total polyhexanide content in the chewing gum composition is released within the first 2 minutes from initiation of a chewing process.

E25. The chewing gum composition of any one of E1-E24, wherein less than 25% of the total polyhexanide content in the chewing gum composition is released within the first 2 minutes from initiation of a chewing process.

E26. The chewing gum composition of any one of E1-E25, wherein greater than 75% of the total polyhexanide content in the chewing gum composition is released within the first 15 minutes from initiation of a chewing process.

E27. The chewing gum composition of any one of E1-E26, wherein the polyhexanide has a weight average molecular weight of between about 1600 g/mol and about 3600 g/mol.

E28. The chewing gum composition of any one of E1-E27, wherein the total weight of the chewing gum composition is between about 1.4 g and about 2.5 g, wherein the total weight of the polyhexanide is between about 2 mg and 50 mg, and wherein the polyhexanide is in the chewing gum core.

E29. The chewing gum composition of any one of E1-E32, further comprising at least one coating layer.

E30. A method of treating an infectious disease of the oral cavity, comprising administering the chewing gum composition of any one of E1-E29.

E31. The method of E30, wherein the infectious disease of the oral cavity is selected from the group consisting of gingivitis, periodontitis, peri-implantitis, dental caries, mycosis, laryngitis, pharyngitis, and halitosis.

E32. The method of E30 or E31, wherein the chewing gum composition is administered between about one and about ten times per day.

E33. The method of any one of E30-E32, wherein the chewing gum composition is administered between about one and about four times per day.

E34. A method of treating a viral infection, comprising administering the chewing gum composition of any one of E1-E29.

E35. A method of preparing the chewing gum composition of any of E1-E29, wherein greater than 75% of the total polyhexanide content in the chewing gum composition is released within 15 minutes from initiation of a chewing process.

E36. A chewing gum composition comprising polyhexanide, wherein the chewing gum composition comprises a chewing gum core, wherein the chewing gum core comprises between about 0.05% and about 10% polyhexanide by weight, and wherein the chewing gum core was formed using a compression force between about 5 kN/cm$^2$ and about 50 kN/cm$^2$.

E37. The chewing gum composition of E36, wherein the chewing gum core was formed using a compression force between about 20 kN/cm$^2$ and about 50 kN/cm$^2$.

E38. A chewing gum composition comprising polyhexanide, wherein the chewing gum composition comprises a chewing gum core, wherein the chewing gum core comprises between about 0.05% and about 10% polyhexanide by weight, and wherein the total weight of the chewing gum composition is between about 1.4 g and about 2.5 g.

E39. The chewing gum composition of E38, wherein the total weight of chewing gum composition is between about 1.6 g and about 2.1 g.

E40. A chewing gum composition comprising polyhexanide, wherein the chewing gum composition comprises a chewing gum core, wherein the chewing gum core comprises between about 0.05% and about 10% polyhexanide by weight, and wherein less than 30% of the total polyhexanide content in the chewing gum composition is released within the first 2 minutes from initiation of a chewing process.

E41. The chewing gum composition of E40, wherein less than 50% of the total polyhexanide content in the chewing gum composition is released within the first 4 minutes from initiation of a chewing process.

E42. The chewing gum composition of E40 or E41, wherein greater than 75% of the total polyhexanide content in the chewing gum composition is released within the first 15 minutes from initiation of a chewing process.

E43. The chewing gum composition of any one of E1-E29, wherein the weight percentage of the total chewing gum core that is water-insoluble is between about 20% and about 50%.

E44. The chewing gum composition of any one of E1-E29, wherein the weight percentage of the total chewing gum core that is water-insoluble is between about 27% and about 40%.

EXAMPLES

The following examples are illustrative and non-limiting, of the products and methods described herein. Suitable modifications and adaptations of the variety of conditions, formulations, and other parameters normally encountered in the field and which are obvious to those skilled in the art in view of this disclosure are within the spirit and scope of the invention.

Example 1

Chewing Gum Core

| Ingredient | Amount (mg) | Weight % |
|---|---|---|
| Health In Gum PWD 03 (gum base) | | 82 |
| PG ALEX 13 T - Lab 2949 (gum base) | | 10 |
| Sucralose | | 0.3 |
| Saccharin | | 0.15 |
| Acesulfame K | | 0.4 |
| Stevia | | 0.2 |
| PHMB and SiO$_2$ | 20 and 1 | 5 |
| Spearmint flavor | | 3.5 |
| Mg stearate | | 2.0 |
| NaHCO$_3$ | | 0.25 |
| CaCO$_3$ | | 0.25 |
| NaF | 0.2 | 0.0095 |
| Total | | 100 |

PHMB was added to SiO$_2$ and ground to a powder. Ingredients in an amount less than 1 weight percent were added together and mixed to form a uniform powder. PHMB and SiO$_2$ and the remaining ingredients were added to the mixture and mixed at room temperature.

The mixture was added to a single punch tablet press (Diaf, Netherlands) to form tablets.

Example 2

Coating Formulation 1—Coating and Blue Menthol Granules

| Ingredient | Amount (g) | Amount per 400 mg | Weight % |
|---|---|---|---|
| Xylitol | 416 | 208 | 52 |
| Mannitol | 136 | 68 | 17 |
| Gum Arabic | 8 | 4 | 1 |
| TiO$_2$ | 8 | 4 | 1 |
| Demineralized water | 232 | 116 | 29 |
| Total | 800 | 400 | 100 |

Flavors Added after 100 mg Coating

| Ingredient | Amount (g) |
| --- | --- |
| Sucralose | 1.0 |
| Spearmint | 2.5 |
| Menthol microgranules | 0.5 |
| Carnauba Wax | 1.0 |
| Total | 5.0 |

Composition of Menthol Microgranules

PUREDELIVERY Pearl 360 Menthol Flavor

| Ingredient | Weight Percentage |
| --- | --- |
| Menthol flavor | 7.7% |
| Sorbitol | 72% |
| Maize maltodextrin | 10% |
| Modified waxy maize starch | 6% |
| Methyl cellulose | 4% |
| Brilliant Blue FCF | 0.3% |

A 50:50 ratio of gum arabic and cold water were mixed. The remaining water was heated in a bowl. Xylitol and mannitol powder were added to the heated water, stirred, and heated to 75° C. The gum arabic and cold water mixture were added to the heated mixture, except for 2-3 grams, which were saved for the initial coat (one dose before suspension). $TiO_2$ was then added. 100 mg of coating was applied to the gum pieces. Then flavors were added and applied to the gum pieces in one or two doses. The total coating per gum piece was 400 mg.

The gums were dried for a minimum of 1 hour after the last flavor dose was added. The gums were then polished with carnauba wax. Actual weight of the cores before coating (10 pieces)=13.0 g. Theoretical weight of the tablets after coating (10 pieces)=17.0 g.

Example 3

Coating Formulation 2

| Ingredient | Amount (g) | Amount per 400 mg | Weight % |
| --- | --- | --- | --- |
| Xylitol | 640 | 208 | 52 |
| Mannitol | 209 | 68 | 17 |
| Gum Arabic | 12.3 | 4 | 1 |
| $TiO_2$ | 12.3 | 4 | 1 |
| Demineralized water | 357 | 116 | 29 |
| Total | 1230 | 400 | 100 |

Flavors and Colors

| Ingredient | Amount (g) |
| --- | --- |
| Stevia | 2.64 |
| Spearmint (flavor) | 1.76 |
| Menthol microgranules | 1.5 |
| Sensipearl Intense Silver (color) | 1.5 |
| Carnauba Wax | 1.23 |
| Sensipearl Intense Silver (color) | 0.82 |
| Total | 5.0 |

A 50:50 ratio of gum arabic and cold water were mixed. The remaining water was heated in a bowl. Xylitol and mannitol powder were added to the heated water, stirred, and heated to 75° C. The gum arabic and cold water mixture were added to the heated mixture. Added $TiO_2$. After preparation of the coating suspension, the coating suspension was sprayed onto the gums in a very small amount until the weight was 2200 mg/10 pieces. Then the Stevia and 10 mL of the coating suspension were mixed together and added to the coating pan. Another 100 mg of coating suspension was poured on the gums (2300 mg/10 pieces) and then the spearmint flavor was added. After another 100 mg of coating was poured on the gums, the menthol microgranules and the silver intense color was added. Finally, the coating pan was cleaned and the gums were polished with a blend of carnauba wax and silver intense color for about 30 minutes.

Actual weight of the cores before coating (10 pieces)=21.0 g. Theoretical weight of the tablets after coating (10 pieces)=24.0 g.

Example 4

Comparative Testing of Different Administration Modes

Materials 8 samples:

Chewing gum, 20 mg, phase sample (analog 30 mg phase sample)

Polyhexanide 0.15% oral rinse (PRONTORAL, B. Braun Melsungen, Germany)

CB 12 chewing gum (Media Company (0.3% Zn and 0.025% chlorhexidine))

Anginosan lozenge (Merz Company, polyhexanide as sole active agent)

Chewing gum, 20 mg, powder sample (20 mg polyhexidine as micronized dry substance in homogeneous mixture with sugar-free, flavored gum base)

Chewing gum, 30 mg, phase sample (30 mg polyhexidine derived from a 20% stock solution for achieving homogeneous distribution in mixture with sugar-free, flavored gum base)

Null reference: 0 mg sample (sugar-free flavored gum base without active agent)

Reference sample: chlorhexidine oral rinse 0.12% (PAROEX, Sunstar Company)

Methods

Eight (8) subjects, double-blind experiment. Last oral hygiene for each subject was 24 hours prior to experiment. Last food intake for each subject was 2 hours prior to swabbing. Conservatively/prosthetically treated, caries free, up to 7/8 fully toothed quadrants having a PSI of up to max II. All chewing gums were chewed for 15 minutes and then discarded. The oral rinses were applied for 30 seconds, each according to the manufacturer's instructions, and then spit out. The lozenge was left in the mouth of each subject until complete dissolution, according to the manufacturer's instructions. Dissolution usually took just under 11 minutes.

Swabs were taken from occlusal surfaces and the sulcus, each contralaterally before (left side)/after (right side) the application, from region 4 to 6. Incubation was carried out on nutrient medium (blood, Columbia agar) for 48 hours under anaerobic conditions.

Visual evaluation of the colonies included number/density, photographic documentation, macro lens, and approximate counting of colony number/area.

Different investigations were carried out concerning the general suitability and determination of an effective formulation for the test substance, polyhexanide, when applied by means of a chewing gum. The 'gold standard' chlorhexidine, which is described in the literature, served as a positive control in the test series for a comparison with other polyhexanide dosage forms and with relevant known products. See Mathur, S., et al., "Clorhexidine: The gold standard in chemical plaque control," *Nat. J. Physiol. Pharm. Pharmacol.* 1(2):45-50 (2011); Balagopal, S., et al., "Chlorhexidine: The gold standard antiplaque agent," *J. Pharm. Sci. & Res.* 5(12):270-274 (2013); C. G. Jones, "Chlorhexidine: is it still the gold standard?" *Periodontology* 15(1):55-62 (1997); Krayer, J. W., et al., "Non-surgical chemotherapeutic treatment strategies for the management of periodontal disease," *Dent. Clin. North Am.* 54(1):13-33 (2010). Polyhexanide is art recognized and well-documented in medicine but is rarely used in dentistry.

Results for the Chewing Gums

The experiments performed demonstrated that a clear detection of aerobic and anaerobic bacterial colonies could be found on the agar media for the control group, i.e., the chewing gum without polyhexanide, both before and after the mastication. The estimated number of bacteria was $10 \times 10^8$ colonies per plate after an anaerobic mastication time of 48 hours in an incubator. When using the 'gold standard' chlorhexidine as a reference, a reduction by 2-log units to a colony density of $10 \times 10^6$ was observed. Mastication with the chewing gum containing 0.026% chlorhexidine did not achieve substantially any reduction in bacterial count. In contrast, polyhexanide containing chewing gum unexpectedly achieved clear bacterial reduction (to $10 \times 10^4$ per agar plate): i.e., reduced by 2-log units compared to the reference standard. In the null hypothesis used in this study, it was assumed that the polyhexanide containing producting would have an effect comparable to polyhexanide.

Results for the Lozenge

When the active agent polyhexanide was administered in the form of a lozenge, no detectable reduction in bacterial count was observed. This was all the more surprising given that the required application time (of more than 5 minutes) was clearly reached or exceeded by the 11 minute exposure time of the lozenges, including that such exposure time was substantially comparable to that for the chewing gum.

General Observations

The effect on occlusal surfaces was higher than on the sulcus area of the teeth. The difference is, advantageously (and unexpectedly), clearly less pronounced with the polyhexanide chewing gum than is the case with both the chlorhexidine and polyhexanide oral rinses, as well as with the chlorhexidine chewing gum.

The effect is concentration dependent up to a total active agent content of 20 mg. Interestingly, higher concentrations do not show a significant enhancement of the bactericidal effect.

Different methods of processing and incorporating the active agent (i.e., differences between the phase and powder), as well as the addition of a surfactant, did not seem to influence the polyhexanide effect.

Example 5

Sensory Impression of Polyhexanide in Mouthwash Versus Chewing Gum

Materials 2 samples:

Polyhexanide mouthwash, 0.15% polyhexanide (PRONTORAL, B. Braun, Melsungen, Germany)

Polyhexanide chewing gum (solid sample), 20 mg polyhexanide

Methods

With the average stimulated saliva production through chewing gum, the polyhexanide-concentration in the oral cavity was similar to that observed with the mouthwash. To exclude the remaining effect of sensory influence by the active ingredient, we let all 24 probands try the mouthwash first and a day or so later, the chewing gum. The mouthwash was used according to the manufacturer's instructions for 30 seconds and the chewing gum was used for 15 minutes.

Probands rated the products using the following scoring system:

1=very good
2=good
3=(still) pleasant
4=(rather) unpleasant
5=bad
6=very bad
7=unacceptable The average score given by the probands was 1.94 (good/very good) for the gum and 4.44 (rather unpleasant/bad) for the mouthwash. Two probands judged the mouthwash as 7 (unacceptable). None of the probands scored the gum worse than 4 (rather unpleasant). 24 probands scored the gum a 3 (still pleasant) or better. 19 probands scored the mouthwash as a 4 (rather unpleasant) or higher. One proband scored the mouthwash better than the gum. None of the probands gave equal scores to the mouthwash and gum.

Using polyhexanide in similar active concentration applied by a chewing gum provided a significantly better sensory result compared to that observed with a mouthwash. The taste of polyhexanide was not tolerable to some probands when applied in a mouthwash; however, this effect was not observed when polyhexanide was applied in a chewing gum.

Example 6

Comparison Testing of 10 mg Polyhexanide Versus 10 mg Chlorhexidine Chewing Gum

The testing of a chewing gum containing 10 mg polyhexanide versus a chewing gum containing 10 mg chlorhexidine was performed to determine if polyhexanide and chlorhexidine have the same or a different antimicrobiological effect when both are added as active ingredient in the same amount using the same technique in identical chewing gum samples. In particular, the goal was to determine if the efficacy of the antibacterial agent chlorhexidine, which is known to be the gold standard and is well-documented, displays the same or different effect in the intraoral environment when used in an identical dosage, incorporation, and application as polyhexanide in the form of a chewing gum.

Materials 2 samples

Chewing gum with 10 mg polyhexanide, sugar-free, flavored gum base (2.4 g)

Chewing gum with 10 mg chlorhexidine, sugar-free, flavored gum base (2.4 g) To minimize variation between the samples, the same gum base (HEALTH IN GUM PWD 04, Cafosa, Spain) and the same production method were used for both samples and, with the exception of mint flavor, no additional excipients were used.

Methods 10 subjects were tested in a double-blind study with numbers allocated to the samples and the numbers were randomly assigned to the test subjects. Last oral hygiene of subjects occurred 24 hours prior to the trial. Last food intake occurred 2 hours prior to the trial. The test accommodated conservatively/prosthetically treated sets of teeth (no removable dentures) with a PSI of up to a maximum of II.

Chewing gums were chewed for 15 minutes and then discarded. Swabs were taken from the sulcus regions, each contralaterally from the left (prior to application) and right (after application) from regions 4 to 6. Samples were applied to blood agar plates, which were assigned to numbers, prior to or after chewing, respectively. Plates were blinded. Samples were incubated on nutrient medium during 48 hours in an incubator under anaerobic conditions. Photographs were taken for all samples prior to and after the chewing gum was chewed by the subjects. The photographs were visually evaluated to approximate the colony number and area.

Results

Assessment of the growth-inhibiting, antibacterial effect was performed using the following scale:

| Semi-quantitative evaluation | Meaning due to picture impression |
|---|---|
| ++ | Swab "after application" shows lower bacterial count than swab "before application" |
| + | Swab "after application" probably shows lower bacterial count than swab "before application" |
| = | Swab "after application" and "before application" show similar bacterial counts |

Samples with 10 mg chlorhexidine achieved the score "+" twice and the score "=" three times. Samples with 10 mg polyhexanide achieved the score "+" once and the score "++" four times. Therefore, with chlorhexidine, the three samples did not achieve a detectable effect and two samples achieved a probable antibacterial effect. With polyhexanide, one sample displayed a probable antibacterial effect and four samples displayed a good antibacterial effect.

It was estimated that samples with the score "+" showed an estimated germ reduction of 1 to 2 log units per agar plate. And, it was estimated that samples with the score "++" showed an estimated germ reduction of up to 4 log units per agar plate.

The results demonstrate that the germ reduction of chlorhexidine was estimated to be 0 up to a maximum of 2 log units (a statistical average of 0.8) and the germ reduction of polyhexanide was estimated to be 1 up to a maximum of 4 log units (a statistical average of 2.7). In conclusion, in chewing gums containing the same dosage of active ingredient, the chewing gum with polyhexanide showed a significantly better antibacterial effect that the chewing gum with chlorhexidine.

Example 7

Dynamic Release Study of the Polyhexanide Chewing Gums

Two batches of chewing gum compositions, Batch 1 and Batch 2, were used to prepare PHMB-containing chewing gums with different weights. The percentage of PHMB was the same in all samples.

Method for quantifying the content and the dynamic release of PHMB from the chewing gums: The analytical method was based on the determination by liquid chromatography coupled by a light scattering detector (ELSD). The dissolution test for the chewing gums (dynamic release) is based on the European Pharmacopoeia guidelines (2.9.25. Dissolution test for medicated chewing gums). The methods were calibrated using PHMB stock solutions, PHMB 100% reference solutions, placebo solutions, and spiked placebo solutions. The method achieved a percentage of recovery of 90.0-110.0% for the PHMB in the tested solutions.

The following test was used to determine the dissolution rate of PHMB in chewing gums: The dissolution rate was determined by applying a mechanical kneading procedure to a piece of gum placed in a small chamber containing 20 mL of phosphate buffer solution (pH=6.2) designed to simulate the process of chewing at medium temperature (37±0.5° C.). The gum was artificially chewed by horizontal pistons, and a vertical piston ensured that the gum stayed in the right place between chews. Machine speed was controlled to ensure a constant cycle. One cycle (chew) was defined as follows: the horizontal pistons started from the outermost position, moved to their innermost position, then returned to their outermost position. Within one cycle, the vertical piston moved from its lowest position to its uppermost position and back to its lowest position. The gum was artificially chewed by the lower and upper chewing surfaces. Machine speed was controlled to ensure a constant cycle. The distance between the lower and upper pistons can be adjusted based on the chewing gum thickness (set 1 mm up to chewing gum thickness). At sampling times of 2, 4, 6, 8, 10, 15, and 20 minutes, the apparatus was stopped, a sample of the dissolution medium was taken, and the content of PHMB was determined. Additional phosphate buffer was added after each sample to maintain a total volume of 20 mL. 6 chewing gums were analyzed for each sample and the mean values are shown in the figures herein.

The sample chewing gums were prepared in an eccentric tablet press machine with a rectangular shape as described in TABLEs 3 and 4.

TABLE 3

| Chewing Gum Compession | |
|---|---|
| Tablet press machine | Korsch EKO |
| Model of Function | Eccentric single station |
| Punch | Rectangular SC 10 × 20 mm |
| Punch manufacturer | Lurga Metalurgica |
| Revolutions per minute | 10 |
| Tablet per hour | 600 |
| Principal Pressure (Kg/cm$^2$) | 3312.4 ± 254.8 kg/cm$^2$ |
| Pre-compression force | N.A. |

TABLE 4

Dimensions of the PHMB Chewing Gums

| PHMB Chewing Gum (grams) | Thickness (mm) | Distance between surfaces (mm) |
|---|---|---|
| 1.05 grams | 5.56 ± 0.15 mm | 2.5 mm |
| 1.6 grams | 7.80 ± 0.15 mm | 4.5 mm |
| 2.1 grams | 9.80 ± 0.15 mm | 5 mm |

Batch 1 was prepared using the composition described in TABLE 5.

TABLE 5

Composition of the Chewing Gums of Batch 1

| Ingredient | Weight % | Weight Per Chewing Gum (mg) | Weight Per 500 Chewing Gums (g) |
|---|---|---|---|
| Core: | | | |
| PHMB | 0.95 | 10.00 | 5.00 |
| SiO (5% of PHMB) | 0.05 | 0.53 | 0.26 |
| Health In Gum PWD 03 (gum base) | 78.94 | 828.87 | 414.43 |
| PG ALEX 13 T - Lab 2949 (gum base) | 10.00 | 105.00 | 52.50 |
| CaCO$_3$ DC | 0.25 | 2.63 | 1.31 |
| NaHCO$_3$ | 0.25 | 2.63 | 1.31 |
| Sucralose | 0.30 | 3.15 | 1.58 |
| Acid Saccharin | 0.15 | 1.58 | 0.79 |
| Acesulfame K | 0.40 | 4.20 | 2.10 |
| Xylitol | 0.20 | 2.10 | 1.05 |
| Flavor 1 | 3.50 | 36.75 | 18.38 |
| NaF | 0.01 | 0.10 | 0.05 |
| Masking flavor | 2.00 | 21.00 | 10.50 |
| Flavor 2 | 1.00 | 10.50 | 5.25 |
| Mg stearate | 2.00 | 21.00 | 10.50 |
| Core Total | 100.00 | 1050.03 | 525.01 |
| Coating: | | | |
| Opadry Experimental No. 190024 Clear | 30.00 | 315.00 | 157.50 |
| Core and Coating Total: | 130.00 | 1365.03 | 682.51 |

Batch 1 was compressed at 3 different sizes (each one at 3 principal pressure of compression) as described in TABLEs 6-8.

TABLE 6

Compression Parameters for Batch 1 - 1050 mg PHMB Chewing Gums

| Weight (mg) | Compression Force Upper Punch (kg/cm$^2$) | Compression Force Lower Punch (kg/cm$^2$) | Average Compression Force (kg/cm$^2$) | Ejection Force (kg/cm$^2$) |
|---|---|---|---|---|
| 1050 | 774.6 | 586.0 | 677.8 (Low CF) | 7139.5 |
| 1050 | 1763.2 | 1600.1 | 1681.7 (Medium CF) | 6736.9 |
| 1050 | 3297.1 | 2527.6 | 2909.8 (High CF) | 7837.6 |

TABLE 7

Compression Parameters for Batch 1 - 1600 mg PHMB Chewing Gums

| Weight (mg) | Compression Force Upper punch (kg/cm$^2$) | Compression Force Lower Punch (kg/cm$^2$) | Average Compression Force (kg/cm$^2$) | Ejection Force (kg/cm$^2$) |
|---|---|---|---|---|
| 1600 | 1110.9 | 876.5 | 993.7 (Low CF) | 8505.2 |
| 1600 | 2038.4 | 1798.9 | 1916.1 (Medium CF) | 9320.6 |
| 1600 | 3297.1 | 2446.1 | 2874.1 (High CF) | 10018.7 |

TABLE 8

Compression Parameters for Batch 1 - 2100 mg PHMB Chewing Gums

| Weight (mg) | Compression Force Upper Punch (kg/cm$^2$) | Compression Force Lower Punch (kg/cm$^2$) | Average Compression Force (kg/cm$^2$) | Ejection Force (kg/cm$^2$) |
|---|---|---|---|---|
| 2100 | 963.1 | 703.2 | 835.7 (Low CF) | 4688.3 |
| 2100 | 1712.3 | 1421.8 | 1564.5 (Medium CF) | 6798.1 |
| 2100 | 3297.1 | 2517.4 | 2904.7 (High CF) | 11073.6 |

Batch 2 was prepared using the composition described in TABLE 9 with the compression parameters described in TABLE 10.

TABLE 9

Composition of the Chewing Gums of Batch 2

| Ingredient | Weight % | Weight Per Chewing Gum (mg) | Weight Per 500 Chewing Gums (g) |
|---|---|---|---|
| Core: | | | |
| PHMB | 0.95 | 10.00 | 5.00 |
| SiO (5% of PHMB) | 0.05 | 0.53 | 0.26 |
| Health In Gum PWD 03 (gum base) | 88.25 | 926.60 | 463.3 |
| CaCO$_3$ DC | 0.25 | 2.63 | 1.31 |
| NaHCOs | 0.25 | 2.63 | 1.31 |
| Sucralose | 0.38 | 4.00 | 2.00 |
| Acid Saccharin | 0.10 | 1.00 | 0.50 |
| Acesulfame K | 0.48 | 5.00 | 2.50 |
| Xylitol | 0.29 | 3.00 | 1.50 |
| Flavor 1 | 3.50 | 36.75 | 18.38 |
| NaF | 0.01 | 0.10 | 0.05 |
| Masking flavor | 2.00 | 21.00 | 10.50 |
| Flavor 2 | 1.00 | 10.50 | 5.25 |
| Menthol granules (DN-841-208-8) | 0.50 | 5.30 | 2.65 |
| Mg stearate | 2.00 | 21.00 | 10.50 |
| Core Total | 100.00 | 1050.03 | 525.01 |
| Coating: | | | |
| Opadry Experimental No. 190024 Clear | 30.00 | 315.00 | 157.50 |
| Core and Coating Total: | 130.00 | 1365.03 | 682.51 |

TABLE 10

Compression Parameters for Batch 2 PHMB Chewing Gums

| Weight (mg) | Compression Force Upper Punch (kg/cm²) | Compression Force Lower Punch (kg/cm²) | Average Compression Force (kg/cm²) | Ejection Force (kg/cm²) |
|---|---|---|---|---|
| 1600 | 3327.7 | 2502.1 | 2925.1 (High CF) | 10044.2 |
| 2100 | 3241.1 | 2456.3 | 2848.7 (High CF) | 10966.6 |

Figure 2:
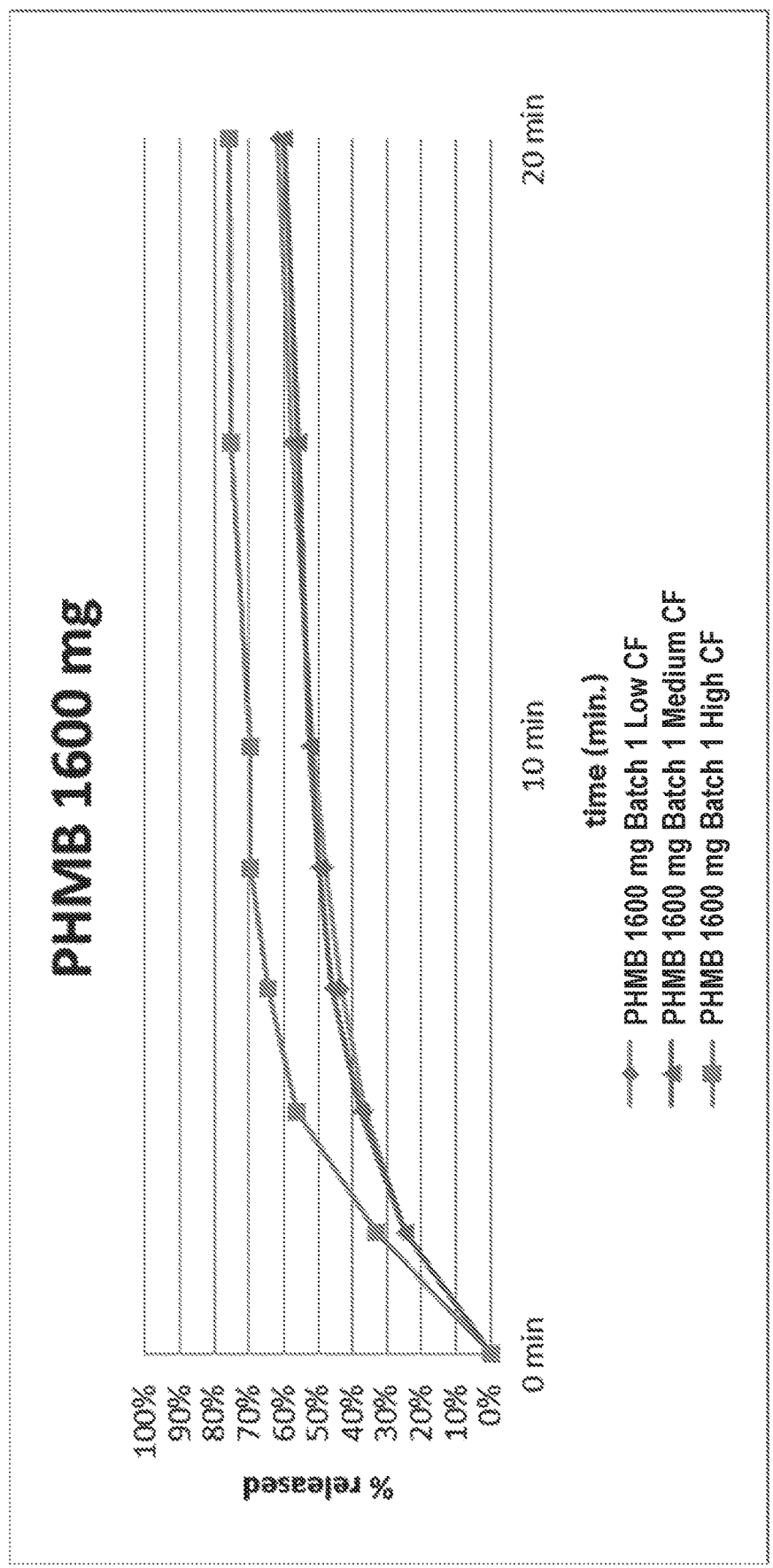
FIG. 2 is a line graph showing the percentage of PHMB released over time for 1600 mg samples of PHMB chewing gums having the composition of Batch 1 as described TABLE 5 in Example 7, compressed at three different compression forces: 994 kg/cm$^2$ (Low CF), 1916 kg/cm$^2$ (Medium CF), and 2874 kg/cm$^2$ (High CF).
Figure 3:
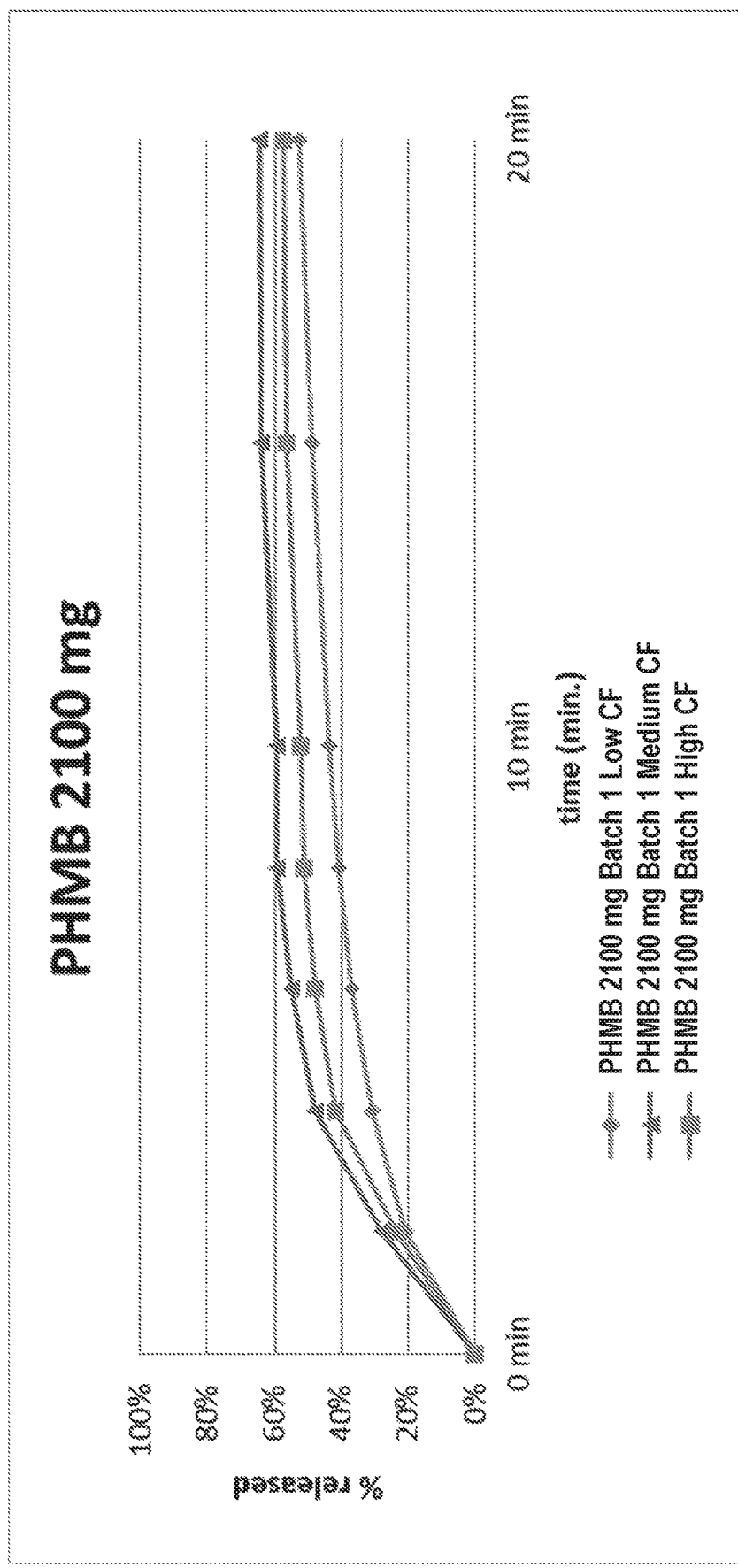
FIG. 3 is a line graph showing the percentage of PHMB released over time for 2100 mg samples of PHMB chewing gums having the composition of Batch 1 as described in TABLE 5 in Example 7, compressed at three different compression forces: 836 kg/cm$^2$ (Low CF), 1564 kg/cm$^2$ (Medium CF), and 2905 kg/cm$^2$ (High CF).
Figure 4:
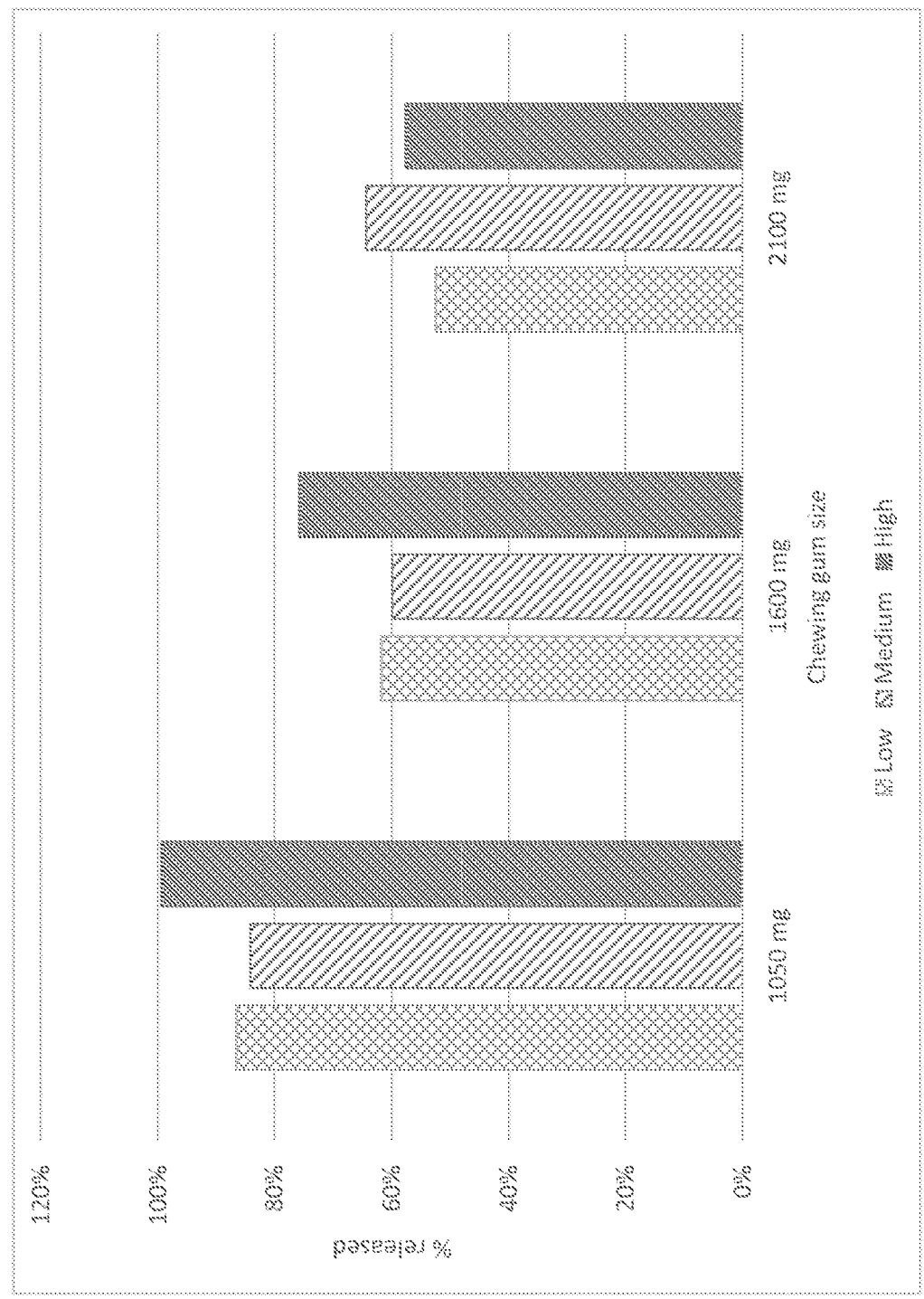
FIG. 4 is a bar graph showing the percentage of PHMB released for 1050 mg, 1600 mg, and 2100 mg sample of PHMB chewing gums having the composition of Batch 1 as described in TABLE 5 in Example 7, compressed as described in TABLEs 6-8 in Example 7 at three different compression forces (Low, Medium, or High).
Figure 5:
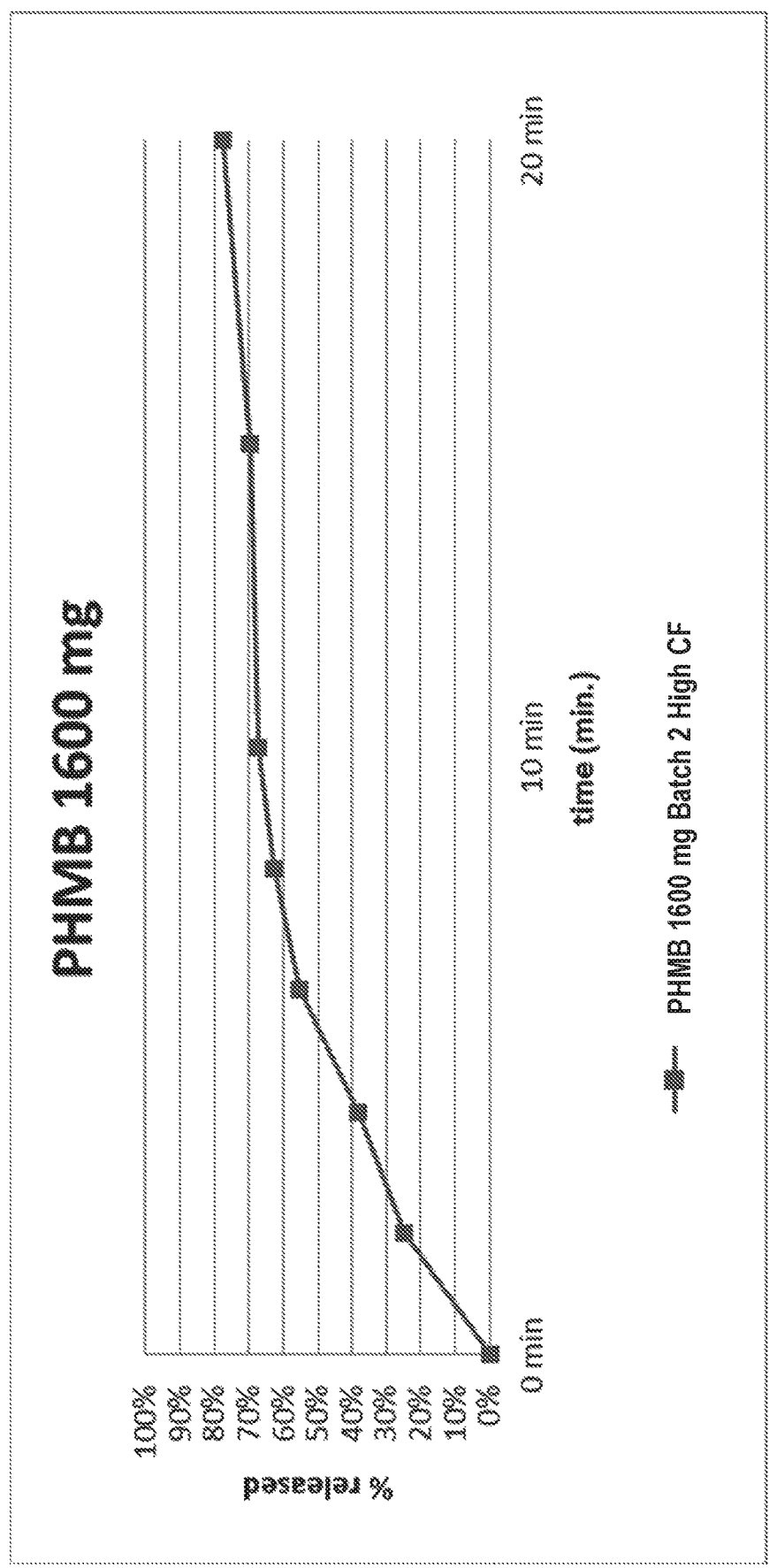
FIG. 5 is a line graph showing the percentage of PHMB released over time for 1600 mg samples of PHMB chewing gums having the composition of Batch 2 as described in TABLE 9 in Example 7, compressed using an average compression force of 2925 kg/cm$^2$ (High CF).
Figure 6:
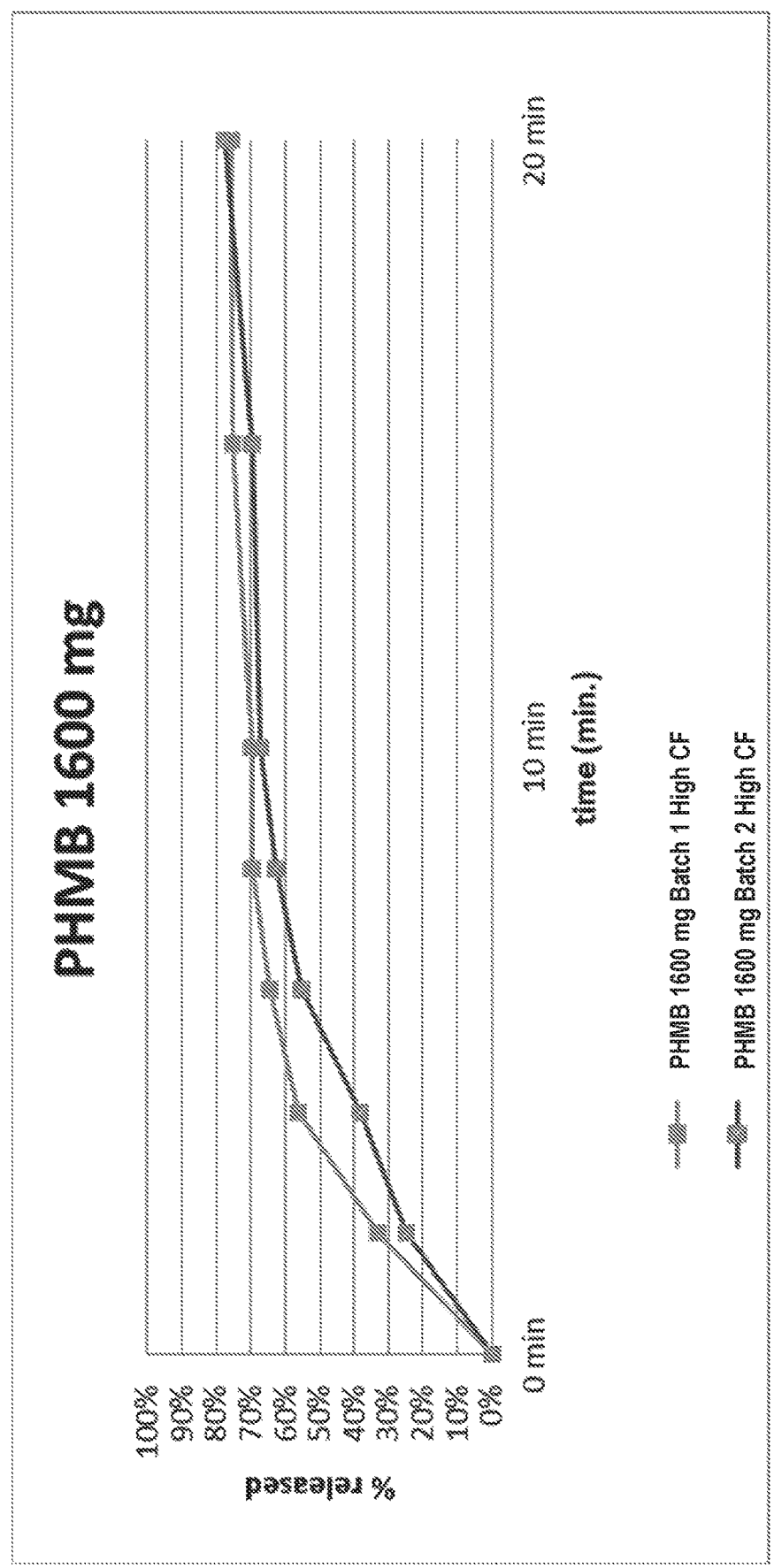
FIG. 6 is a line graph comparing the percentage of PHMB released over time for a 1600 mg sample of PHMB chewing gum having the composition of Batch 1 as described in TABLE 6 of Example 7, compressed using an average compression force of 2874 kg/cm$^2$ (High CF) and a 1600 mg sample of PHMB chewing gum containing the composition of Batch 2 as described in TABLE 9 of Example 7, compressed using an average compression force of 2925 kg/cm$^2$ (High CF).
Figure 7:
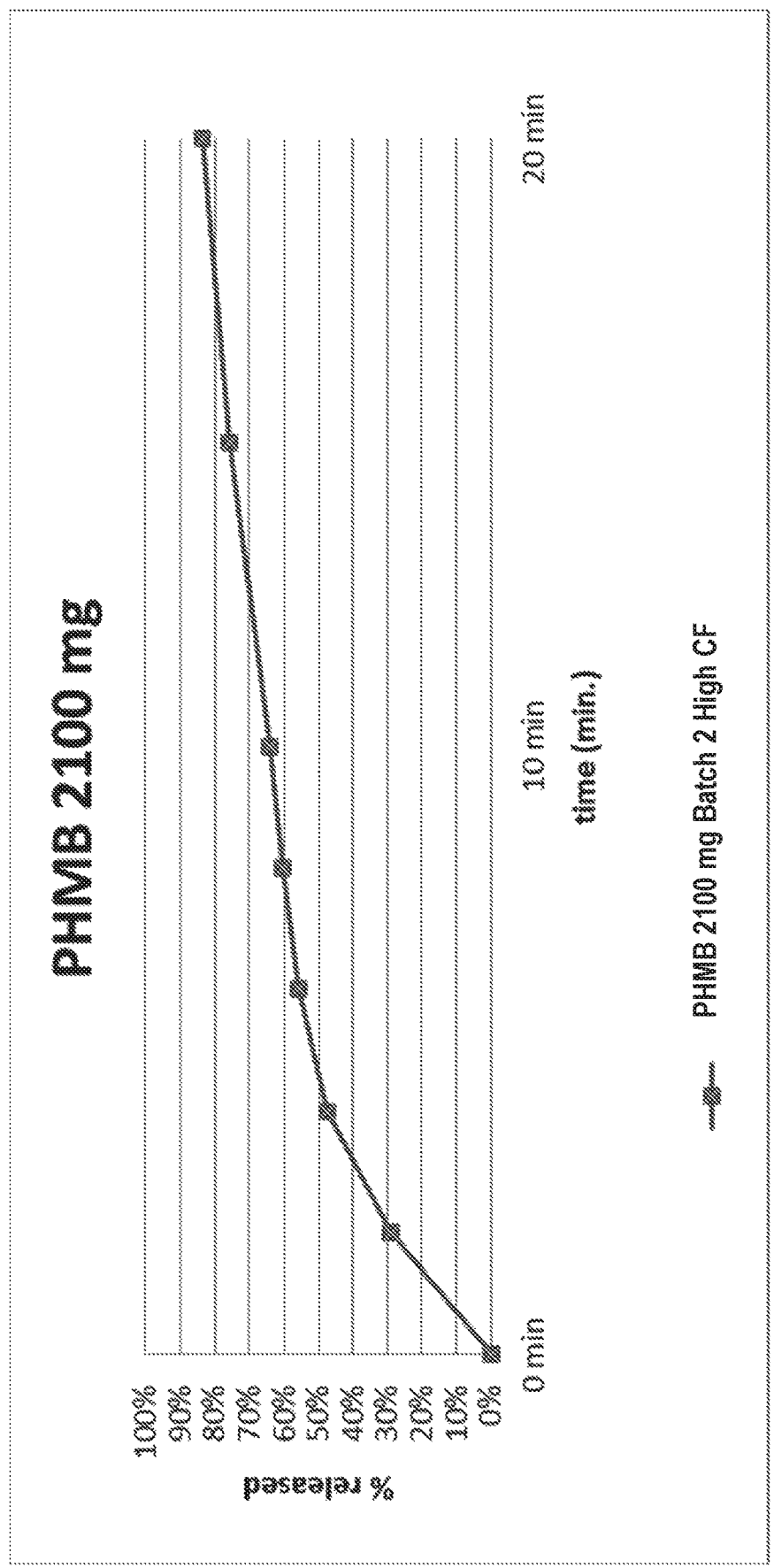
FIG. 7 is a line graph showing the percentage of PHMB released over time for a 2100 mg sample of PHMB chewing gum having the composition of Batch 2 as described in TABLE 9 of Example 7, compressed using an average compression force of 2849 kg/cm$^2$ (High CF)
Figure 8:
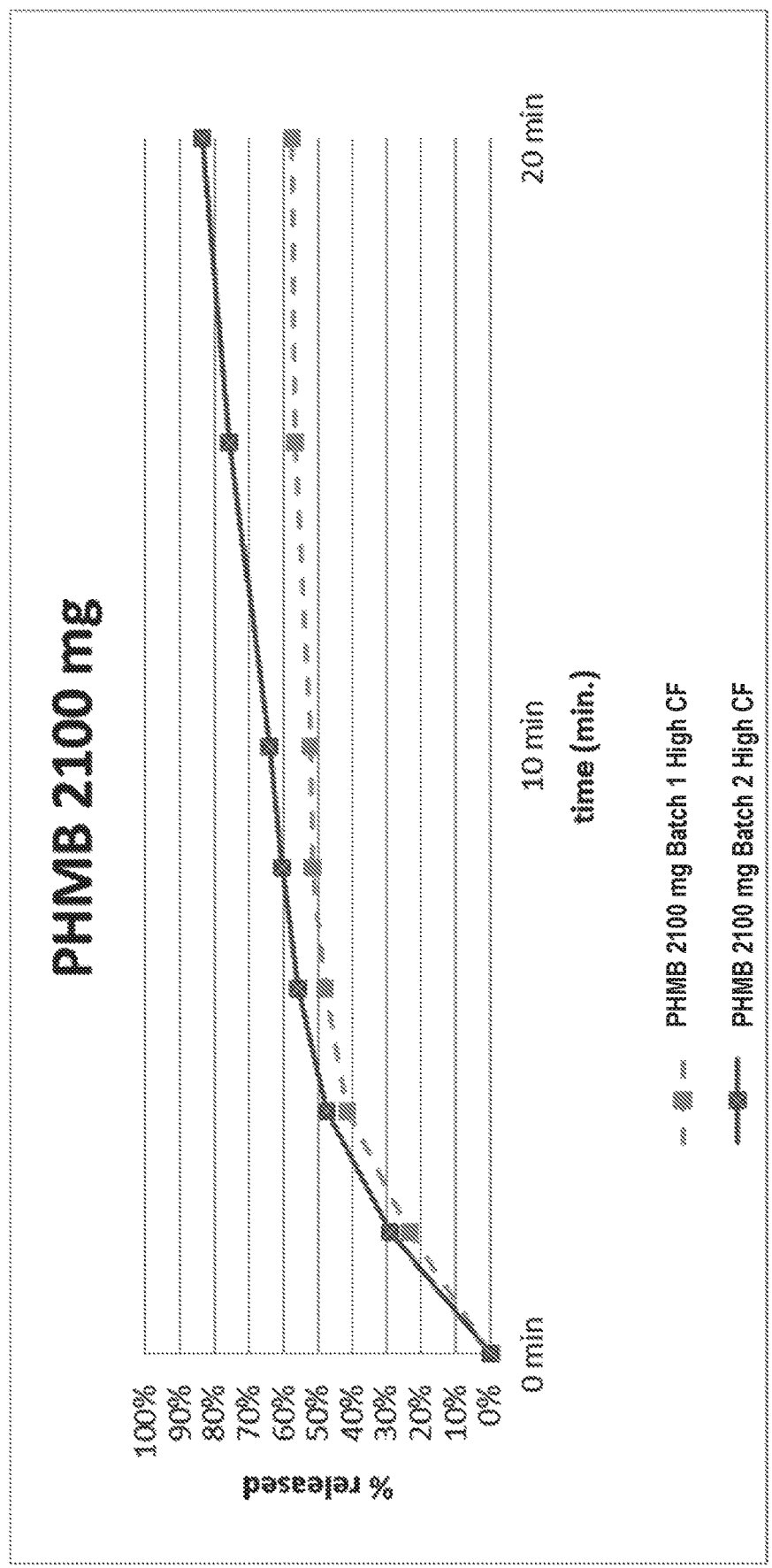
FIG. 8 is a line graph comparing the percentage of PHMB released over time for a 2100 mg sample of PHMB chewing gum having the composition of Batch 1 as described in TABLE 6 of Example 7, compressed using an average compression force of 2905 kg/cm$^2$ (High CF) and a 2100 mg sample of PHMB chewing gum containing the composition of Batch 2 described in TABLE 9 of Example 7, compressed using an average compression force of 2849 kg/cm$^2$ (High CF).

Results are shown in FIGS. 1-8. The relative release was inversely proportional to the amount of gumbase; that is, the higher the amount of gumbase, the lower the amount of API that was released. Surprisingly, the highest compression force improved the active release, i.e. resulted in a faster release and release of higher amounts of API.

While various embodiments have been described above, it should be understood that they have been presented by way of example only, and not limitation. It will be apparent to persons skilled in the relevant art that various changes in form and detail can be made therein without departing from the spirit and scope of the invention. Thus, the breadth and scope should not be limited by any of the above-described exemplary embodiments, but should be defined only in accordance with the following claims and their equivalents.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A chewing gum composition comprising polyhexanide, wherein the chewing gum composition comprises a chewing gum core, and wherein the chewing gum core comprises between about 0.05% and about 10% polyhexanide by weight, wherein between about 15% and about 60% by weight of the chewing gum core is water-insoluble, further wherein the chewing gum composition comprises gum base with a weight between about 100 mg and about 5 g, wherein less than 50% of the polyhexanide in the chewing gum composition is released within 2 minutes from initiation of a chewing process, wherein the release of the polyhexanide is controlled by the water-insoluble content of the chewing gum core and the weight of the gum base, and wherein the chewing gum core is formed using a compression force of between about 20 kN/cm² and about 50 kN/cm².

2. The chewing gum composition of claim 1, further comprising a fluoride salt.

3. The chewing gum composition of claim 2, wherein the fluoride salt is selected from the group consisting of sodium fluoride, potassium fluoride, stannous fluoride, potassium stannous fluoride, lithium fluoride, ammonium fluoride, tin fluoride, indium fluoride, zirconium fluoride, copper fluoride, nickel fluoride, palladium fluoride, zinc fluoride, ammonium fluoride, stannous chloroflouride, sodium monofluorophosphate, ammonium monofluorophosphate, aluminum monofluorophosphate, and mixtures thereof.

4. The chewing gum composition of claim 2, wherein the chewing gum core comprises between about 0.001% and about 0.10% of the fluoride salt by weight.

5. The chewing gum composition of claim 1, further comprising at least one sweetener.

6. The chewing gum composition of claim 1, further comprising at least one flavor.

7. The chewing gum composition of claim 1, further comprising at least one filler.

8. The chewing gum composition of claim 1, wherein the chewing gum core comprises between about 5% to about 95% of the at least one gum base by weight.

9. The chewing gum composition of claim 1, wherein less than 25% of the polyhexanide in the chewing gum composition is released within 2 minutes from initiation of a chewing process.

10. The chewing gum composition of claim 1, wherein greater than 75% of the polyhexanide in the chewing gum composition is released within 15 minutes from initiation of a chewing process.

11. The chewing gum composition of claim 1, wherein the polyhexanide has a weight average molecular weight of between about 1600 g/mol and about 3600 g/mol.

12. The chewing gum composition of claim 1, wherein the total weight of the chewing gum composition is between about 1.4 g and about 2.5 g, wherein the total weight of the polyhexanide is between about 2 mg and 50 mg, and wherein the polyhexanide is in the chewing gum core.

13. The chewing gum composition of claim 1, further comprising at least one coating layer.

14. The chewing gum composition of claim 1, wherein between about 20% and about 50% of the chewing gum core is water-insoluble.

15. A chewing gum composition comprising polyhexanide, wherein the chewing gum composition comprises a chewing gum core comprising between about 0.05% and about 10% polyhexanide by weight, wherein the chewing gum composition has a total weight between about 1.4 g and about 2.5 g, wherein less than 50% of the polyhexanide in the chewing gum composition is released within 2 minutes from initiation of a chewing process, wherein the release of the polyhexanide is controlled by the water-insoluble content of the chewing gum core and the weight of gum base, and wherein the chewing gum core is formed using a compression force of between about 20 kN/cm² and about 50 kN/cm².

16. A chewing gum composition comprising polyhexanide, wherein the chewing gum composition comprises a chewing gum core comprising between about 0.05% and about 10% polyhexanide by weight, and wherein less than 30% of the polyhexanide in the chewing gum composition is released within 2 minutes from initiation of a chewing process, wherein the chewing gum composition comprises gum base with a weight between about 100 mg and about 5 g, and wherein the release of the polyhexanide is controlled by the water-insoluble content of the chewing gum core and the weight of the gum base, and wherein the chewing gum core is formed using a compression force of between about 20 kN/cm² and about 50 kN/cm².

17. The chewing gum composition of claim 16, wherein less than 50% of the polyhexanide in the chewing gum composition is released within 4 minutes from initiation of a chewing process.

18. The chewing gum composition of claim 16, wherein greater than 75% of the polyhexanide content in the chewing gum composition is released within 15 minutes from initiation of a chewing process.

19. A method of treating an infectious disease of the oral cavity, comprising administering the chewing gum composition of claim 1 to a subject in need thereof.

20. The method of claim 19, wherein the infectious disease of the oral cavity is selected from the group consisting of gingivitis, periodontitis, peri-implantitis, dental caries, mycosis, laryngitis, pharyngitis, and halitosis.

* * * * *